US011219769B2

(12) United States Patent
Ghosh

(10) Patent No.: US 11,219,769 B2
(45) Date of Patent: Jan. 11, 2022

(54) NONINVASIVE METHODS AND SYSTEMS OF DETERMINING THE EXTENT OF TISSUE CAPTURE FROM CARDIAC PACING

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 1268 days.

(21) Appl. No.: 15/142,176

(22) Filed: Apr. 29, 2016

(65) Prior Publication Data

US 2017/0246461 A1 Aug. 31, 2017

Related U.S. Application Data

(60) Provisional application No. 62/300,675, filed on Feb. 26, 2016.

(51) Int. Cl.
*A61N 1/37* (2006.01)
*A61N 1/365* (2006.01)
(Continued)

(52) U.S. Cl.
CPC ............ *A61N 1/3712* (2013.01); *A61B 5/282* (2021.01); *A61B 5/349* (2021.01); *A61B 5/366* (2021.01);
(Continued)

(58) Field of Classification Search
CPC .......... A61B 2562/046; A61B 5/04085; A61B 5/0452; A61B 5/0472; A61B 5/4836;
(Continued)

(56) References Cited

U.S. PATENT DOCUMENTS 4,233,987 A 11/1980 Feingold
4,402,323 A 9/1983 White
(Continued)

FOREIGN PATENT DOCUMENTS

CN 1043621 A 7/1990
CN 1253761 A 5/2000
(Continued)

OTHER PUBLICATIONS

Biffi et al., "Occurrence of Phrenic Nerve Stimulation in Cardiac Resynchronization Therapy Patients: the Role of Left Ventricular Lead Type and Placement Site," *Europace*, 2013; 15:77-82.
(Continued)

*Primary Examiner* — Christopher L Cook
(74) *Attorney, Agent, or Firm* — Mueting Raasch Group

(57) ABSTRACT

Methods and systems of evaluating cardiac pacing in candidate patients for cardiac resynchronization therapy and cardiac resynchronization therapy patients are disclosed. The methods and systems disclosed allow treatments to be personalized to patients by measuring the extent of tissue capture from cardiac pacing under various therapy parameter conditions. Systems and methods of optimizing right ventricle only cardiac pacing are also disclosed.

27 Claims, 17 Drawing Sheets

(51) Int. Cl.
   *A61B 5/00*    (2006.01)
   *A61B 5/282*   (2021.01)
   *A61B 5/349*   (2021.01)
   *A61B 5/366*   (2021.01)
   *A61N 1/04*    (2006.01)
   *A61N 1/05*    (2006.01)
   *A61N 1/362*   (2006.01)
   *A61N 7/00*    (2006.01)

(52) U.S. Cl.
   CPC .......... *A61B 5/4836* (2013.01); *A61B 5/6823* (2013.01); *A61N 1/0476* (2013.01); *A61N 1/056* (2013.01); *A61N 1/3625* (2013.01); *A61N 1/36507* (2013.01); *A61N 7/00* (2013.01); *A61B 2562/046* (2013.01); *A61N 2007/0004* (2013.01); *A61N 2007/0026* (2013.01)

(58) Field of Classification Search
   CPC .... A61B 5/6823; A61N 1/0476; A61N 1/056; A61N 1/3625; A61N 1/36507; A61N 1/3712; A61N 2007/0004; A61N 2007/0026; A61N 7/00
   See application file for complete search history.

(56) References Cited

U.S. PATENT DOCUMENTS

| | | | |
|---|---|---|---|
| 4,428,378 A | 1/1984 | Anderson et al. | |
| 4,497,326 A | 2/1985 | Curry | |
| 4,566,456 A | 1/1986 | Koning et al. | |
| 4,593,702 A | 6/1986 | Kepski | |
| 4,674,511 A | 6/1987 | Cartmell | |
| 4,763,660 A | 8/1988 | Kroll et al. | |
| 4,777,955 A | 10/1988 | Brayten et al. | |
| 4,787,389 A | 11/1988 | Tarjan | |
| 4,979,507 A | 12/1990 | Heinz et al. | |
| 5,052,388 A | 10/1991 | Sivula et al. | |
| 5,054,496 A | 10/1991 | Wen et al. | |
| 5,311,873 A | 5/1994 | Savard et al. | |
| 5,331,960 A | 7/1994 | Lavine | |
| 5,334,220 A | 8/1994 | Sholder | |
| 5,443,492 A | 8/1995 | Stokes et al. | |
| 5,485,849 A | 1/1996 | Panescu et al. | |
| 5,514,163 A | 5/1996 | Markowitz et al. | |
| 5,552,645 A | 9/1996 | Weng | |
| 5,628,778 A | 5/1997 | Kruse et al. | |
| 5,671,752 A | 9/1997 | Sinderby et al. | |
| 5,683,429 A | 11/1997 | Mehra | |
| 5,683,432 A | 11/1997 | Goedeke et al. | |
| 5,687,737 A | 11/1997 | Branham et al. | |
| 5,810,740 A | 9/1998 | Paisner | |
| 5,876,336 A | 3/1999 | Swanson et al. | |
| 5,891,045 A | 4/1999 | Albrecht et al. | |
| 5,922,014 A | 7/1999 | Warman et al. | |
| 6,055,448 A | 4/2000 | Anderson et al. | |
| 6,128,535 A | 10/2000 | Maarse et al. | |
| 6,141,588 A | 10/2000 | Cox et al. | |
| 6,187,032 B1 | 2/2001 | Ohyu et al. | |
| 6,205,357 B1 | 3/2001 | Ideker et al. | |
| 6,226,542 B1 | 5/2001 | Reisfeld | |
| 6,236,883 B1 | 5/2001 | Ciaccio et al. | |
| 6,243,603 B1 | 6/2001 | Ideker et al. | |
| 6,246,898 B1 | 6/2001 | Vesely et al. | |
| 6,301,496 B1 | 10/2001 | Reisfeld | |
| 6,311,089 B1 * | 10/2001 | Mann ............ | A61N 1/368 607/30 |
| 6,330,476 B1 | 12/2001 | Ben-Haim et al. | |
| 6,358,214 B1 | 3/2002 | Tereschouk | |
| 6,377,856 B1 | 4/2002 | Carson | |
| 6,381,493 B1 | 4/2002 | Stadler et al. | |
| 6,393,316 B1 | 5/2002 | Gillberg et al. | |
| 6,418,346 B1 | 7/2002 | Nelson et al. | |
| 6,439,236 B1 | 8/2002 | Porter et al. | |
| 6,442,433 B1 | 8/2002 | Linberg | |
| 6,456,867 B2 | 9/2002 | Reisfeld | |
| 6,473,638 B2 | 10/2002 | Ferek-Petric | |
| 6,480,745 B2 | 11/2002 | Nelson et al. | |
| 6,484,118 B1 | 11/2002 | Govari | |
| 6,507,756 B1 | 1/2003 | Heynen et al. | |
| 6,532,379 B2 | 3/2003 | Stratbucker | |
| 6,584,343 B1 | 6/2003 | Ransbury et al. | |
| 6,599,250 B2 | 7/2003 | Webb et al. | |
| 6,625,482 B1 | 9/2003 | Panescu et al. | |
| 6,640,136 B1 | 10/2003 | Helland et al. | |
| 6,650,927 B1 | 11/2003 | Keidar | |
| 6,766,189 B2 | 7/2004 | Yu et al. | |
| 6,772,004 B2 | 8/2004 | Rudy | |
| 6,804,555 B2 | 10/2004 | Warkentin | |
| 6,847,836 B1 | 1/2005 | Sujdak | |
| 6,856,830 B2 | 2/2005 | He | |
| 6,882,882 B2 | 4/2005 | Struble et al. | |
| 6,885,889 B2 | 4/2005 | Chinchoy | |
| 6,915,149 B2 | 7/2005 | Ben-Haim | |
| 6,968,237 B2 | 11/2005 | Doan et al. | |
| 6,975,900 B2 | 12/2005 | Rudy et al. | |
| 6,978,184 B1 | 12/2005 | Marcus et al. | |
| 6,980,675 B2 | 12/2005 | Evron et al. | |
| 7,013,176 B2 | 3/2006 | Ding et al. | |
| 7,016,719 B2 | 3/2006 | Rudy et al. | |
| 7,031,777 B2 | 4/2006 | Hine et al. | |
| 7,058,443 B2 | 6/2006 | Struble | |
| 7,062,315 B2 | 6/2006 | Koyrakh et al. | |
| 7,092,759 B2 | 8/2006 | Nehls et al. | |
| 7,142,922 B2 | 11/2006 | Spinelli et al. | |
| 7,184,835 B2 | 2/2007 | Kramer et al. | |
| 7,215,998 B2 | 5/2007 | Wesselink et al. | |
| 7,286,866 B2 | 10/2007 | Okerlund et al. | |
| 7,308,297 B2 | 12/2007 | Reddy et al. | |
| 7,308,299 B2 | 12/2007 | Burrell et al. | |
| 7,313,444 B2 | 12/2007 | Pianca et al. | |
| 7,321,677 B2 | 1/2008 | Evron et al. | |
| 7,346,381 B2 | 3/2008 | Okerlund et al. | |
| 7,398,116 B2 | 7/2008 | Edwards | |
| 7,426,412 B1 | 9/2008 | Schecter | |
| 7,454,248 B2 | 11/2008 | Burrell et al. | |
| 7,499,743 B2 | 3/2009 | Vass et al. | |
| 7,509,170 B2 | 3/2009 | Zhang et al. | |
| 7,565,190 B2 | 7/2009 | Okerlund et al. | |
| 7,587,074 B2 | 9/2009 | Zarkh et al. | |
| 7,599,730 B2 | 10/2009 | Hunter et al. | |
| 7,610,088 B2 | 10/2009 | Chinchoy | |
| 7,610,092 B2 | 10/2009 | Cowan et al. | |
| 7,613,500 B2 | 11/2009 | Vass et al. | |
| 7,616,993 B2 | 11/2009 | Müssig et al. | |
| 7,664,550 B2 | 2/2010 | Eick et al. | |
| 7,684,863 B2 | 3/2010 | Parikh et al. | |
| 7,742,629 B2 | 6/2010 | Zarkh et al. | |
| 7,747,047 B2 | 6/2010 | Okerlund et al. | |
| 7,751,882 B1 | 7/2010 | Helland | |
| 7,769,451 B2 | 8/2010 | Yang et al. | |
| 7,778,685 B2 | 8/2010 | Evron et al. | |
| 7,778,686 B2 | 8/2010 | Vass et al. | |
| 7,787,951 B1 | 8/2010 | Min | |
| 7,813,785 B2 | 10/2010 | Okerlund et al. | |
| 7,818,040 B2 | 10/2010 | Spear et al. | |
| 7,848,807 B2 | 12/2010 | Wang | |
| 7,860,580 B2 | 12/2010 | Falk et al. | |
| 7,894,889 B2 | 2/2011 | Zhang | |
| 7,912,544 B1 | 3/2011 | Min et al. | |
| 7,917,214 B1 | 3/2011 | Gill et al. | |
| 7,941,213 B2 | 5/2011 | Markowitz et al. | |
| 7,953,475 B2 | 5/2011 | Harlev et al. | |
| 7,953,482 B2 | 5/2011 | Hess | |
| 7,983,743 B2 | 7/2011 | Rudy et al. | |
| 7,996,063 B2 | 8/2011 | Vass et al. | |
| 7,996,070 B2 | 8/2011 | van Dam et al. | |
| 8,010,194 B2 | 8/2011 | Muller | |
| 8,019,402 B1 | 9/2011 | Kryzpow et al. | |
| 8,019,409 B2 | 9/2011 | Rosenberg et al. | |
| 8,032,229 B2 | 10/2011 | Gerber et al. | |
| 8,036,743 B2 | 10/2011 | Savage et al. | |
| 8,060,185 B2 | 11/2011 | Hunter et al. | |

(56) References Cited

U.S. PATENT DOCUMENTS

| | | |
|---|---|---|
| 8,126,547 B2 | 2/2012 | Kramer et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,321,020 B1 * | 11/2012 | Bornzin .............. A61N 1/3704 607/27 |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,909,332 B2 | 12/2014 | Vitali et al. |
| 8,948,869 B2 | 2/2015 | Ghosh et al. |
| 8,965,489 B2 | 2/2015 | Ghosh |
| 8,972,228 B2 | 3/2015 | Ghosh et al. |
| 9,031,642 B2 | 5/2015 | Ghosh |
| 9,037,238 B2 | 5/2015 | Stadler et al. |
| 9,132,274 B2 | 9/2015 | Ghosh |
| 9,155,897 B2 | 10/2015 | Ghosh et al. |
| 9,186,515 B2 | 11/2015 | Ramanathan et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,408,549 B2 | 8/2016 | Brockway et al. |
| 9,474,457 B2 | 10/2016 | Ghosh et al. |
| 9,486,151 B2 | 11/2016 | Ghosh et al. |
| 9,510,763 B2 | 12/2016 | Ghosh et al. |
| 9,526,435 B2 | 12/2016 | Ghosh |
| 9,572,505 B2 | 2/2017 | Ghosh et al. |
| 9,586,050 B2 | 3/2017 | Ghosh et al. |
| 9,586,052 B2 | 3/2017 | Gillberg et al. |
| 9,610,045 B2 | 4/2017 | Du et al. |
| 9,737,223 B2 | 8/2017 | Du et al. |
| 9,750,941 B2 | 9/2017 | Ghosh |
| 9,782,094 B2 | 10/2017 | Du et al. |
| 10,166,396 B2 | 1/2019 | Schrock et al. |
| 10,687,722 B2 | 6/2020 | Du et al. |
| 10,695,352 B2 | 6/2020 | Chopra et al. |
| 10,780,279 B2 | 9/2020 | Ghosh |
| 2002/0087089 A1 | 7/2002 | Ben-Haim |
| 2002/0001613 A1 | 10/2002 | Yu et al. |
| 2002/0143264 A1 | 10/2002 | Ding et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0022063 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0014913 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0118181 A1 * | 5/2007 | Sathaye .............. A61N 1/3712 607/28 |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0249585 A1 | 10/2008 | Lippert et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0000843 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0027093 A1 | 10/2009 | Yonce et al. |
| 2009/0254140 A1 | 10/2009 | Rosenberg et al. |
| 2009/0270729 A1 | 10/2009 | Corbucci et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min |
| 2010/0174137 A1 | 7/2010 | Shim |
| 2010/0198292 A1 | 8/2010 | Honeck et al. |
| 2010/0022813 A1 | 9/2010 | Chen |
| 2010/0234916 A1 | 9/2010 | Turcott et al. |
| 2010/0249622 A1 | 9/2010 | Olson |

(56) References Cited

U.S. PATENT DOCUMENTS

| | | | |
|---|---|---|---|
| 2010/0249860 A1* | 9/2010 | Shuros | A61N 1/3625 607/4 |
| 2010/0254583 A1 | 10/2010 | Chan et al. | |
| 2010/0268059 A1 | 10/2010 | Ryu et al. | |
| 2011/0004111 A1 | 1/2011 | Gill et al. | |
| 2011/0004264 A1 | 1/2011 | Siejko et al. | |
| 2011/0009918 A1 | 1/2011 | Bornzin et al. | |
| 2011/0022112 A1 | 1/2011 | Min | |
| 2011/0054286 A1 | 3/2011 | Crosby | |
| 2011/0054559 A1 | 3/2011 | Rosenberg et al. | |
| 2011/0054560 A1 | 3/2011 | Rosenberg et al. | |
| 2011/0075896 A1 | 3/2011 | Matsumoto | |
| 2011/0092809 A1 | 4/2011 | Nguyen et al. | |
| 2011/0112398 A1 | 5/2011 | Zarkh et al. | |
| 2011/0118803 A1 | 5/2011 | Hou et al. | |
| 2011/0137369 A1 | 6/2011 | Ryu et al. | |
| 2011/0144510 A1 | 6/2011 | Ryu et al. | |
| 2011/0172728 A1 | 7/2011 | Wang | |
| 2011/0190615 A1 | 8/2011 | Phillips et al. | |
| 2011/0201915 A1 | 8/2011 | Gogin et al. | |
| 2011/0213260 A1 | 9/2011 | Keel et al. | |
| 2011/0264158 A1* | 10/2011 | Dong | A61B 5/7264 607/9 |
| 2011/0319954 A1 | 12/2011 | Niazi et al. | |
| 2012/0004567 A1 | 1/2012 | Eberle et al. | |
| 2012/0101543 A1 | 4/2012 | Demmer et al. | |
| 2012/0101546 A1 | 4/2012 | Stadler et al. | |
| 2012/0203090 A1 | 8/2012 | Min | |
| 2012/0253419 A1 | 10/2012 | Rosenberg et al. | |
| 2012/0002963 A1 | 11/2012 | Zhang et al. | |
| 2012/0283587 A1 | 11/2012 | Ghosh et al. | |
| 2012/0284003 A1* | 11/2012 | Gosh | A61B 5/0402 703/2 |
| 2012/0296388 A1 | 11/2012 | Zhang et al. | |
| 2012/0302904 A1 | 11/2012 | Lian et al. | |
| 2012/0303084 A1 | 11/2012 | Kleckner et al. | |
| 2012/0310297 A1 | 12/2012 | Sweeney | |
| 2012/0330179 A1 | 12/2012 | Yuk et al. | |
| 2013/0006332 A1 | 1/2013 | Sommer et al. | |
| 2013/0018250 A1 | 1/2013 | Caprio et al. | |
| 2013/0018251 A1 | 1/2013 | Caprio et al. | |
| 2013/0030491 A1 | 1/2013 | Stadler et al. | |
| 2013/0060298 A1 | 3/2013 | Splett et al. | |
| 2013/0072790 A1 | 3/2013 | Ludwig et al. | |
| 2013/0096446 A1 | 4/2013 | Michael et al. | |
| 2013/0116739 A1 | 5/2013 | Brada et al. | |
| 2013/0131529 A1 | 5/2013 | Jia et al. | |
| 2013/0131749 A1 | 5/2013 | Sheldon et al. | |
| 2013/0131751 A1 | 5/2013 | Stadler et al. | |
| 2013/0136035 A1 | 5/2013 | Bange et al. | |
| 2013/0150913 A1 | 6/2013 | Bornzin et al. | |
| 2013/0165983 A1 | 6/2013 | Ghosh et al. | |
| 2013/0165988 A1 | 6/2013 | Ghosh | |
| 2013/0184697 A1* | 7/2013 | Han | A61B 18/18 606/33 |
| 2013/0261471 A1 | 10/2013 | Saha et al. | |
| 2013/0261688 A1 | 10/2013 | Dong et al. | |
| 2013/0289640 A1 | 10/2013 | Zhang et al. | |
| 2013/0296726 A1 | 11/2013 | Niebauer et al. | |
| 2013/0304407 A1 | 11/2013 | George et al. | |
| 2013/0324828 A1 | 12/2013 | Nishiwaki et al. | |
| 2014/0005563 A1 | 1/2014 | Ramanathan et al. | |
| 2014/0018872 A1 | 1/2014 | Siejko et al. | |
| 2014/0135866 A1 | 5/2014 | Ramanathan et al. | |
| 2014/0135867 A1* | 5/2014 | Demmer | A61N 1/3686 607/28 |
| 2014/0163633 A1 | 6/2014 | Ghosh et al. | |
| 2014/0222099 A1 | 8/2014 | Sweeney | |
| 2014/0236252 A1 | 8/2014 | Ghosh et al. | |
| 2014/0027723 A1 | 9/2014 | Ghosh | |
| 2014/0275928 A1 | 9/2014 | Acquista et al. | |
| 2014/0276125 A1 | 9/2014 | Hou et al. | |
| 2014/0323882 A1 | 10/2014 | Ghosh et al. | |
| 2014/0323892 A1 | 10/2014 | Ghosh et al. | |
| 2014/0323893 A1 | 10/2014 | Ghosh et al. | |
| 2014/0371807 A1 | 12/2014 | Ghosh et al. | |
| 2014/0371808 A1 | 12/2014 | Ghosh et al. | |
| 2014/0371832 A1 | 12/2014 | Ghosh et al. | |
| 2014/0371833 A1 | 12/2014 | Ghosh et al. | |
| 2015/0032016 A1 | 1/2015 | Ghosh | |
| 2015/0032171 A1 | 1/2015 | Ghosh | |
| 2015/0032172 A1 | 1/2015 | Ghosh | |
| 2015/0032173 A1 | 1/2015 | Ghosh | |
| 2015/0045849 A1 | 2/2015 | Ghosh et al. | |
| 2015/0142069 A1 | 5/2015 | Sambelashvili | |
| 2015/0157225 A1 | 6/2015 | Gillberg et al. | |
| 2015/0157231 A1 | 6/2015 | Gillberg et al. | |
| 2015/0157232 A1 | 6/2015 | Gillberg et al. | |
| 2015/0157865 A1 | 6/2015 | Gillberg et al. | |
| 2015/0216434 A1 | 8/2015 | Ghosh et al. | |
| 2015/0265840 A1 | 9/2015 | Ghosh et al. | |
| 2016/0030747 A1 | 2/2016 | Thakur et al. | |
| 2016/0030751 A1 | 2/2016 | Ghosh et al. | |
| 2016/0045737 A1 | 2/2016 | Ghosh et al. | |
| 2016/0045738 A1 | 2/2016 | Ghosh et al. | |
| 2016/0045744 A1 | 2/2016 | Ghosh et al. | |
| 2016/0175598 A1* | 6/2016 | Volpe | A61N 1/046 607/4 |
| 2016/0184590 A1 | 6/2016 | Gosh | |
| 2017/0246461 A1 | 8/2017 | Ghosh | |
| 2018/0199843 A1 | 7/2018 | Ghosh et al. | |
| 2019/0143117 A1 | 5/2019 | Ghosh | |
| 2019/0183370 A1 | 6/2019 | Gillberg et al. | |

FOREIGN PATENT DOCUMENTS

| | | |
|---|---|---|
| CN | 1878595 A | 12/2006 |
| CN | 101073502 A | 11/2007 |
| CN | 203425379 | 2/2014 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |

(56) References Cited

FOREIGN PATENT DOCUMENTS

| WO | WO 2013/010165 A1 | 1/2013 |
|---|---|---|
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" *J. Am. Coll. Cardiol.* 2011; 58:1893-1902.
Czerwinskas et al., "Method of Segmentation of Thorax Organs Images Applied to Modeling the Cardiac Electrical Field," *Engineering in Medicine and Biology Society*, Proceedings of the 22nd Annual International Conference of the IEEE, vol. 1, 23, Jul. 23, 2000.; pp. 402-405.
Dawoud, F et al., "Inverse Electrocardiographic Imaging to Assess Electrical Dyssynchrony in Cardiac Resynchronization Therapy Patients," *Computing in Cardiology*, 2012; 39:993-996.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5): 692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9): 1469-1475.
"Heart Failure Management" datasheet [online], Medtronic, Minneapolis, Minnesota, [Last updated on Jun. 3, 2013].Retrieved from the Internet: www.medtronic.com; 9 pages.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," *Annals of Biomedical Engineering*, vol. 38, No. 3, Mar. 2010, pp. 865-875.
Miri et al., "Comparison of the electrophysiologically based optimization methods with different pacing parameters in patient undergoing resynchronization treatment," $30^{th}$ *Annual International IEEE EMBS Conference*, Aug. 2008, pp. 1741-1744.
Miri et al., "Computerized Optimization of Biventricular Pacing Using Body Surface Potential Map," $31^{st}$ *Annual International Conference of the IEEE EMBS*, Sep. 2009, pp. 2815-2818.
Miri et al., "Efficiency of Timing Delays and Electrode Positions in Optimization of Biventricular Pacing: A Simulation Study," *IEEE Transactions on Biomedical Engineering*, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms : a simulation study," *Circulation Research*, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-634.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52, Available online Apr. 24, 2012.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Wang et al., "Application of the Method of Fundamental Solutions to Potential-based Inverse Electrocardiography," *Annals of Biomedical Engineering*, Aug. 2006, pp. 1272-1288.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
Botker MD, PhD., et al., "Electromechanical Mapping for Detection of Myocardial Viability in Patients with ischemia Cardiomyopathy," Circulation, Mar. 2001; vol. 103, No. 12, pp. 1631-1637.

(56) References Cited

OTHER PUBLICATIONS

Fung et al., Chapter 20, Optimization of Cardiac Resynchronization Therapy, Cardiac Resynchronization Therapy, Second Edition, Copyright 2008, Blackwell Publishing Ltd., pp. 356-373.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Nash et al., "An Experimental-Computational Framework for Validating in-vivo ECG Inverse Algorithms," International Journal of Bioelectromagnetism, vol. 2, No. 2, Dec. 31, 2000, 9 pp.
Sweeney et al., QRS Fusion Complex Analysis Using Wave Interference to Predict Reverse Remodeling During Cardiac Resynchronization Therapy, heart Rhythm, 2014, 11:806-813.
Wellens, MD et al., "The Electrocardiogram 102 Years After Einthoven," Circulation, Feb. 2004; vol. 109, No. 5, pp. 562-564.
(PCT/US2017/019004) PCT Notification of Transmittal of the International Search Report and the Written Opinion of the International Searching Authority, or the Declaration, dated Jun. 7, 2017, 12 pages.
Anatomy and Physiology: Chapter 19, "The Cardiovascular System: The Heart", accessed online at https://opentextbc.ca/anatomyandphsiology/chapter/19-2-cardiac-cycle/, 2013.
Aquilina, "A brief history of cardiac pacing", Images Paediatr Cardiol, Apr.-Jun. 2006, pp. 17-81.
Beck et al., "50th Anniversary of the first successful permanent implantation in the United States: historical review and future directions", Am J Cardiol, Sep. 15, 2010, pp. 810-818.
Freund et al., "A Decision-Theoretic Generalization of Online Learning and an Application to Boosting," Journal of Computer and System Sciences, 1997; 55(1):119-139.
Friedman, "Greedy Function Approximation: A Gradient Boosting Machine," Annals of Statistics, 2001; 29 (5):1189-1232.
Friedman, "Stochastic Gradient Boosting," Computational Statistics and Data Analysis, 2002; 38(4):367-378.
Friedman et al., "Additive Logistic Regression: a Statistical View of Boosting," Annals of Statistics, 2000; 28 (2):337-374.
Livneh et al., "Extracorporeal Acute Cardiac Pacing by High Intensity Focused Ultrasound", Progress in Biophysics and Molecular Biology, 115, 2014.
Ridgeway, "The State of Boosting," Computing Science and Statistics, 1999; 31:172-181.

\* cited by examiner

NONINVASIVE METHODS AND SYSTEMS OF DETERMINING THE EXTENT OF TISSUE CAPTURE FROM CARDIAC PACING

CROSS-REFERENCE TO RELATED APPLICATIONS

This application is related to commonly owned U.S. patent application Ser. No. 15/142,118, titled "METHODS AND SYSTEMS OF OPTIMIZING RIGHT VENTRICULAR ONLY PACING FOR PATIENTS WITH RESPECT TO AN ATRIAL EVENT AND LEFT VENTRICULAR EVENT" filed on the same day herewith, now U.S. Pat. No. 10,780,279, which is incorporated herein by reference in its entirety.

In addition, this application claims the benefit of U.S. Provisional Application No. 62/300,675, filed on Feb. 26, 2016. The disclosure of the above application is incorporated herein by reference in its entirety.

BACKGROUND

Doctors and other medical professionals may evaluate performance characteristics of the heart to provide individualized treatment to patients using cardiac resynchronization therapy. The beat of the heart is controlled by the sinoatrial node (SA node), a group of conductive cells located in the right atrium near the entrance of the superior vena cava. A depolarization signal generated by the SA node activates the atrioventricular node (AV node). The AV node briefly delays the propagation of the depolarization signal, allowing blood in the atria to drain into the ventricles, before passing the depolarization signal to the ventricles of the heart. The coordinated contraction of both ventricles drives the flow of blood through the torso of a patient. In certain circumstances, the conduction of the depolarization signal from the AV node to the left and right ventricles may be interrupted or slowed. This may result in a dyssynchrony in the contraction of the left and right ventricles, and eventually in heart failure or death.

Cardiac Resynchronization Therapy (CRT) may correct the symptoms of electrical dyssynchrony by providing pacing therapy to one or both ventricles or atria, e.g., by providing pacing to encourage earlier activation of the left or right ventricles. By pacing the contraction of the ventricles, the ventricles may be controlled so that the ventricles contract in synchrony. Some patients undergoing CRT have experienced improved ejection fraction, increased exercise capacity, and an improved feeling of well-being.

Providing CRT to a patient may involve determining whether the patient will derive benefit from the CRT prior to implantation of a cardiac rhythm device. Additionally, detailed evaluations may aid in determining optimal placement of one or more ventricular pacing leads or optimal programming of device parameters, such as selection of electrodes on multi-polar right or left ventricular leads, as well as selection of the timing of the pacing pulses delivered to the electrodes, such as atrioventricular (A-V) and intraventricular (V-V) delays.

SUMMARY

Methods and systems of evaluating cardiac pacing in candidate patients for cardiac resynchronization therapy and cardiac resynchronization therapy patients are disclosed.

In one aspect, the present disclosure provides a method of determining the extent of applied cardiac tissue stimulation due to pacing. The method includes applying electrodes on a patient's torso, pacing the patient's cardiac tissue, receiving torso-surface potential signals detected by the electrodes, determining an activation time for each electrode, determining the number of electrodes that register an activation time that meets predetermined criteria, calculating a percentage index by dividing the number of electrodes that registered an activation time that meets a predetermined criteria by the total number of electrodes distributed on the patient's torso, determining the extent of applied cardiac tissue stimulation due to pacing based on the percentage index.

In one or more embodiments, the method includes pacing the cardiac tissue to avoid interference with the intrinsic rhythm of the heart. Further, the predetermined criteria may be a predetermined activation time threshold. The predetermined criteria may be a predetermined time period within which the activation time of electrodes must be registered. For example, the predetermined time period may be about 5 ms, 10 ms, 15 ms, or 20 milliseconds from a specified time origin where the specified time origin is the earliest activation time detected for a corresponding depolarization cycle. The predetermined time period may also be a percentile of the activation-times registered by the electrodes.

In one or more embodiments, the method may include adjusting a therapeutic parameter value based on the extent of applied cardiac tissue electrical stimulation due to pacing. The therapeutic parameter may include the magnitude of the energy applied by the pacing source. Additionally, the therapeutic parameter may be the direction of a pacing vector applied by the pacing source. The direction of the pacing vector may be determined from the geometry of the device.

In one or more embodiments, the system to determine the extent of applied cardiac tissue stimulation due to pacing includes electrodes configured to be distributed on a patent's torso, a pacing device configured to stimulate the patent's cardiac tissue, a processing unit configured to determine the number of electrodes that register an activation time that meet as predetermined criteria, calculate a percentage index by dividing the number of electrodes that registered activation times that meet the predetermined criteria by the total number of electrodes distributed on the patient's torso and determine the extent of applied cardiac tissue stimulation due to pacing based on the percentage index.

In one or more embodiments, the distributed electrodes include at least 20 electrodes. Additionally, in one or more embodiments, the pacing device is implanted in the patient and comprises a lead in direct contact with cardiac tissue. The pacing device may include a processing unit. The pacing device may also include two electrodes located on the same lead. The pacing device may communicate wirelessly with the processing unit.

In one or more embodiments, the pacing device may be an external device for applying pacing using an ultrasound wave.

In one or more embodiments, the method of determining the extent of applied cardiac tissue stimulation due to pacing may include applying stimulation to the patient's cardiac tissue and receiving potential signals detected at a first time period, determining the extent of applied cardiac tissue stimulation due to pacing based on activation times derived from the potential signals received at the first time period, adjusting a therapeutic parameter related to the delivery of the stimulation to the patient's cardiac tissue based on the determined extent of applied cardiac tissue electrical stimulation due to pacing, in order to meet a predetermined treatment goal applying stimulation to the patient's cardiac tissue and receiving potential signals detected at a second time period determining the extent of applied cardiac tissue stimulation due to pacing based on the potential signals received at the second time period, determining if the adjustment of the therapeutic parameter resulted in meeting the predetermined treatment goal.

In one or more embodiments, the therapeutic parameter may be the magnitude of the energy applied by the pacing source. In one or more embodiments, the therapeutic parameter is the direction of a pacing vector applied by the pacing source. The direction of the pacing vector may be determined from the geometry of a pacing device. Additionally, in one or more embodiments, the therapeutic parameter may be a timing interval between successive stimulations of the cardiac tissue.

In one or more embodiments, the predetermined treatment goal may include increasing the extent of applied cardiac tissue stimulation due to pacing within a predetermined time period. In one or more embodiments, the predetermined treatment goal may include decreasing the extent of applied cardiac tissue stimulation due to pacing within a predetermined time period.

In one or more embodiments, a system to determine the extent of applied cardiac tissue stimulation due to pacing may include electrodes configured to be distributed on a patent's torso, a means for stimulating the patent's cardiac tissue, a means for determining the number of electrodes that register an activation time that meet as predetermined criteria, a means for calculating a percentage index by dividing the number of electrodes that registered activation times that meet the predetermined criteria by the total number of electrodes distributed on the patient's torso, and a means for determining the extent of applied cardiac tissue stimulation due to pacing based on the percentage index.

In one or more embodiments, the means for stimulating the patent's cardiac tissue is implanted in the patient. In one or more embodiments, the means for stimulating the patent's cardiac tissue is external to the patient's body. In one or more embodiments, the means for determining the extent of applied cardiac tissue stimulation due to pacing is implanted in the patient. In one or more embodiments, the means for determining the extent of applied cardiac tissue stimulation due to pacing is external to the patient's body.

In one or more embodiment, a method of determining the extent of applied cardiac tissue stimulation due to pacing includes applying electrodes on a patient's torso, pacing the patient's cardiac tissue, the pacing of the cardiac tissue is timed to avoid interference with the intrinsic rhythm of the heart, receiving torso-surface potential signals detected by the electrodes, determining an activation time for each electrode, determining the number of electrodes that register an activation time that meets a predetermined criteria, calculating a percentage index by dividing the number of electrodes that registered an activation time that meets the predetermined criteria, the predetermined criteria comprises a predetermined time period within which the activation time of electrodes must be registered, by the total number of electrodes distributed on the patient's torso, determining the extent of applied cardiac tissue stimulation due to pacing based on the percentage index.

The present disclosures will aid in assessing the effectiveness of various treatment method, devices, and parameters by allowing health care providers to non-invasively assess the amount of cardiac tissue capture during treatment. Further, non-invasive methods or techniques of stimulating cardiac tissue in combination with the methods and systems disclosed herein will enable patient's cardiac functions to be analyzed without the need for invasive surgery.

BRIEF DESCRIPTION OF THE DRAWINGS/FIGURES

DETAILED DESCRIPTION

Figure 1:
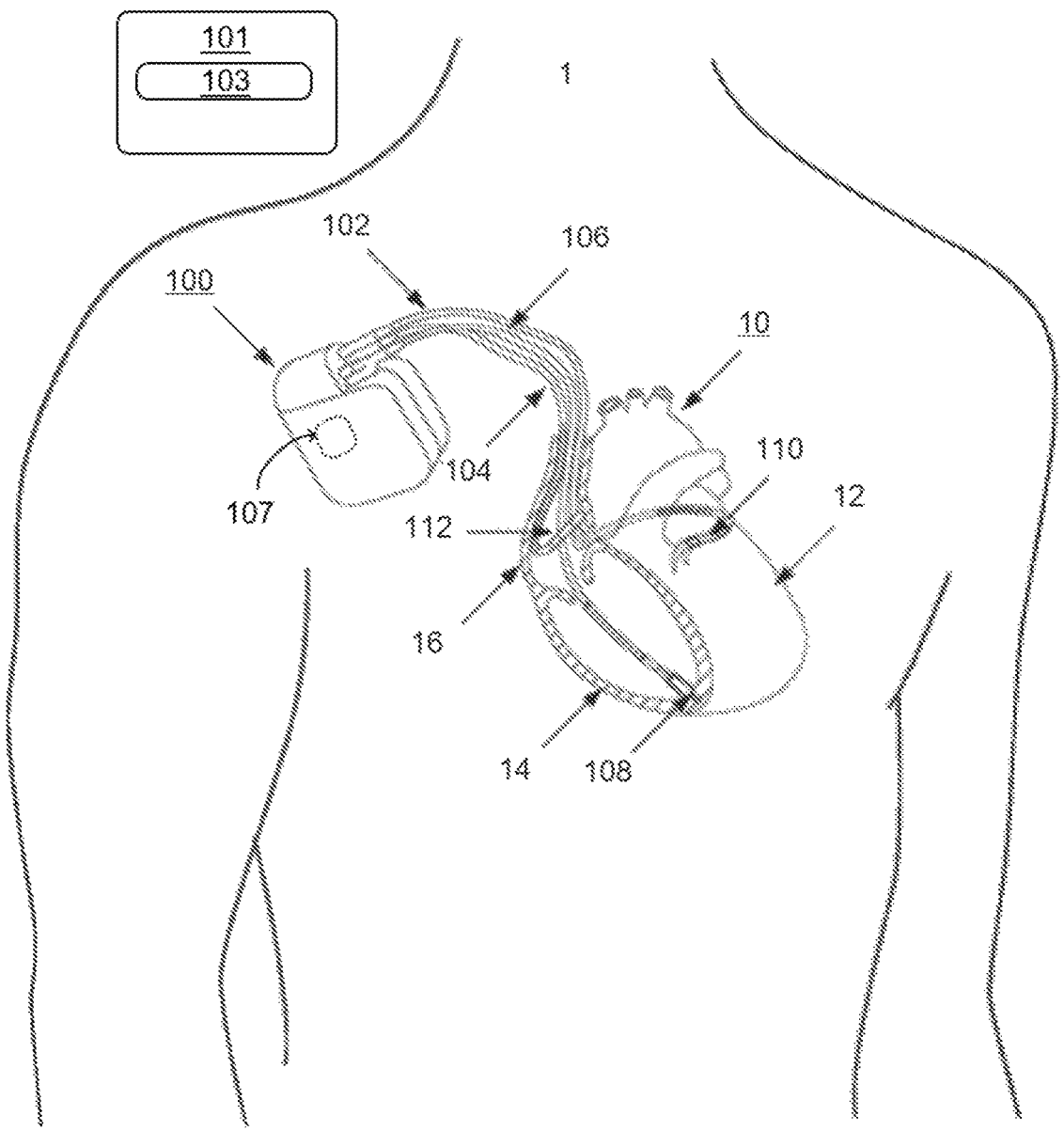
FIG. 1 is a conceptual diagram illustrating an example system that may be used to provide CRT to a heart of a patient.

The present disclosure is directed to methods and systems for evaluating the performance of a heart using a multi-electrode electrocardiogram (ECG). Additionally, the present disclosure is directed to methods and systems of optimizing right ventricular only cardiac pacing.

Assessment of electrical dyssynchrony for these purposes has typically involved assessing QRS duration clinically.

Though CRT is typically recommended for patients with wide QRS duration, hemodynamic improvements through CRT have been reported in narrow QRS heart failure patients. Thus, some patients who may benefit from CRT may not be prescribed CRT based on present electrical dyssynchrony evaluation techniques. The methods and systems disclosed herein are directed to techniques for evaluating electrical dyssynchrony in the heart of a patient, the amount of activation of heart tissue in response to pacing, and methods and systems to optimize CRT therapy.

Evaluating the performance of the heart requires particular systems for mapping heart performance characteristics. For example, a set of electrodes may be spatially distributed about the torso of a patient. The electrodes may each sense a body surface potential signal, and more particularly a torso-surface potential signal, which indicates the depolarization signals of the heart of the patient after the signals have progressed through the torso of the patient. Due to the spatial distribution of the electrodes, the torso-surface potential signal recorded by each electrode may indicate the depolarization of a different spatial region of the heart. Additionally, the strength or other signal characteristics may be recorded.

In some examples, an activation time is determined for each torso-surface potential signal, i.e., for each electrode of the set. The dispersion or sequence of these activation times may be analyzed or presented to provide a variety of indications of the electrical dyssynchrony of the heart of the patient. For example, isochrone or other activation maps of the torso-surface illustrating the activation times may be presented to a doctor or other medical professional to illustrate electrical dyssynchrony of the heart. In some examples, values of one or more statistical indices indicative of the temporal and/or spatial distribution of the activation times may be determined. Such maps and indices, or other indications of dyssynchrony determined based on the torso-surface activation times, may indicate electrical dyssynchrony of the heart to a user, and facilitate evaluation of a patient for CRT, and configuration of CRT for the patient. In some embodiments of the present invention, the extent of applied cardiac stimulation in response to CRT may be evaluated by comparing the number of activating torso-surface electrodes to the total number of torso-surface electrodes. The extent of applied cardiac stimulation in a specific section of the heart may be determined. That is, the extent of applied cardiac stimulation in a specific area of the heart, for example, the left ventricle, may be determined using similar methods.

In some examples, the locations of all or a subset of the electrodes, and thus the locations at which the torso-surface potential signals are sensed, may be projected on the surface of a model torso that includes a model heart. The inverse problem of electrocardiography may be solved to determine electrical activation times for regions of the model heart based on the torso-surface potential signals sensed from the patient. In this manner, the electrical activity of the heart of the patient may be estimated. Various isochrone or other activation time maps of the surface of the model heart may be generated based on the torso-surface potential signals sensed on the surface of the torso of the patient. Further, values of one or more indices indicative of the temporal and/or spatial distribution of the activation times on model heart may be determined. These measures and representations of electrical dyssynchrony may be used to evaluate the suitability of the patient for CRT, adjust the positioning of the CRT leads during implantation, or determine which electrodes of one or more multi-polar leads should be utilized for delivery of CRT, as well as the timing of pacing pulses, such as atrioventricular (A-V) and intra-ventricular (V-V) delays for delivery of CRT to the patient.

For example, the one or more indications of dyssynchrony may be determined or generated based on data collected both during intrinsic conduction and during CRT. The degree of dyssynchrony during intrinsic conduction and CRT may be compared, e.g., to determine whether a patient is a candidate for CRT. Similarly, the one or more indications of dyssynchrony may be determined or generated based on data collected during CRT with different lead positions, different electrode configurations, and/or different CRT parameters, e.g., A-V or V-V delay. The change in dyssynchrony attributable to these different lead positions, different electrode configurations, and/or different CRT parameters may be evaluated.

Some patients receiving CRT have right heart conduction delays. Right heart conduction delays may be caused by right bundle branch blocks or by non-specific interventricular conduction disorders. Right heart conduction delays result in a dyssynchrony in the ventricles of the heart. The dyssynchrony may cause additional stress on the heart and may lead to heart failure and death. When the dyssynchrony and the conduction delay is only in the right ventricle but not in the left ventricle, the condition may be potentially ameliorated by pacing the right ventricle at appropriate timing to achieve synchronization with conduction in the left heart which leads to reduction in global electrical heterogeneity during ventricular depolarization (QRS). Global electrical heterogeneity may be quantified by measures of dispersion of electrical activation times over the entire heart which may include statistical measures like mean, variance, standard deviation, range or inter-quartile deviation applied to activation times which may be measured by noninvasive body-surface mapping techniques. The disclosure herein is also directed to pacing the right ventricle in response to an atrial signal at an atrioventricular (AV) delay time determined as a percentage of the delay between the atrial signal and the left ventricle activation. Methods and systems of optimizing the atrioventricular delay time for right ventricular signal only pacing are also disclosed.

The details of one or more aspects of the disclosure are set forth in the accompanying drawings and the description below. Other features, objects, and advantages will be apparent from the description and drawings, and from the claims.

The effectiveness of CRT depends on many factors including the positioning of the CRT leads during implantation, the use of one or more multi-polar leads the timing of pacing pulses, such as atrioventricular (A-V) and intra-ventricular (V-V) delays for delivery of CRT to the patient. Various systems and devices can be used for sensing bioelectric data from a human body. For example, multi-electrode electrocardiogram (ECG) systems can be utilized for body-surface potential mapping by recording simultaneous ECG measurements from multiple sensors or electrodes applied to selected locations of a patient's body. These sensors may be included in apparatus such as vests, bands, belts, straps, patches, wearable garments, t-shirts, bras, hats (e.g., for neural signals), etc.

Some ECG systems include multiple sensors generally arranged as part of a vest that is attached to a patient. These vests can be applied to a patient's torso for receiving bioelectric signals and, in some configurations, delivering stimulating signals to the patient. Bioelectric signals from the patient are detected by the sensors and transmitted via conductive paths to a medical monitoring system or apparatus such as an ECG base unit.

For example, one type of electrode vest is described in U.S. Pat. No. 6,055,448 to Anderson et al., entitled SENSOR DEVICE. The described device includes a plurality of finger-like substrate portions of a flexible dielectric material that are releasably attachable to the thoracic region of a human body.

Further, for example, U.S. Patent Publication No. 2013/0018251 to Caprio et al., entitled SENSOR DEVICE WITH FLEXIBLE JOINTS, describes a sensor device that includes a flexible dielectric substrate, a plurality of sensors distributed on the substrate, and an electrically conductive network distributed on the substrate connecting the sensors to a terminal portion of the substrate. Integrated flexible joints permit a certain amount of elasticity in and allow relative movement between at least two of the sensors when the sensor device is placed onto the human body.

Such vests are generally provided in multiple sizes to accommodate various body types and sizes of patients. For example, U.S. Patent Publication No. 2011/0190615 to Phillips et al., entitled ELECTRODE PATCH MONITORING DEVICE, describes an electrode patch monitoring device that includes an array of electrodes formed on a flexible substrate. The electrode patch monitoring device may be available in a plurality of sizes.

U.S. Pat. No. 8,972,228 to Subham et al., entitled ASSESSING INTRA-CARDIAC ACTIVATION PATTERNS, incorporated herein in its entirety by reference, describes a sensor system and techniques that use electrodes to determine the characteristics of the heart when the heart is stimulated. The techniques described aid in evaluating cardiac electrical dyssynchrony.

Further U.S. Patent Application No. 62/152,684 entitled METHOD FOR EFFICIENT DELIVERY OF MULTI-SITE PACING, incorporated herein in its entirety by reference, describes systems, methods, apparatuses, and techniques relating to the delivering of electrical stimulation to the heart.

FIG. 1 is a conceptual diagram illustrating an example system that may be used to provide CRT to heart 10 of patient 1. The system may include an implantable medical device (IMD) 100. IMD 100 may be a CRT pacemaker or CRT defibrillator. IMD 100 may be equipped with one or more leads; leads 102, 104, and 106; that are inserted into or on the surface of the left ventricle 12, right ventricle 14, or right atrium 16 of heart 10. Leads 102, 104, and 106 may be equipped with one or more electrodes 108, 110, and 112. IMD 100 may include a processing unit 107.

Heart 10 may suffer from an electrical dyssynchrony. Electrical dyssynchrony may occur when the depolarization signals that start the contraction of ventricles 12 and 14 do not reach the ventricles in a coordinated manner, which results in an inefficient pumping action of heart 10. Patient 1 may experience symptoms of heart failure. Electrical dyssynchrony may be caused by damage to the electrical system of heart 10, e.g., a bundle branch block or damage to the fascicle of heart 10. Alternate conduction pathways may form within heart 10, but these pathways may slow the progress of the electrical depolarization signal and result in the asynchronous contraction of ventricles 12 and 14.

IMD 100 may provide CRT stimulation to heart 10 of patient 1. IMD 100 is depicted as being configured to deliver stimulation to right atrium 16, right ventricle 14, and left ventricle 12 of heart 10. In other examples, IMD 100 may be configured to deliver stimulation to other portions of heart 10 depending on the condition of patient 1. IMD 100 may interact with an external programmer (not shown) to adjust operating characteristics, such as A-V and V-V delays, of the therapy delivered by IMD 100. In some examples, IMD 100 may also be configured to sense the electrical activity of heart 10 through the electrodes on one or more of leads 102, 104, and 106.

As shown in FIG. 1, leads 102, 104, 106 may extend into the heart 10 of patient 1 to deliver electrical stimulation to heart 10 and synchronize the contraction of ventricles 12 and 14. Right ventricular lead 106 extends through one or more veins (not shown), the superior vena cava (not shown), and right atrium 16, and into right ventricle 14. Left ventricular coronary sinus lead 102 extends through one or more veins, the vena cava, right atrium 16, and into the coronary sinus (not shown) to a region adjacent to the free wall of left ventricle 12 of heart 10. Right atrial lead 104 extends through one or more veins and the vena cava, and into the right atrium 16 of heart 10.

In other configurations, IMD 100 may be equipped with more or fewer leads, depending on the requirements of the therapy provided to patient 1. For example, IMD 100 may be equipped with leads that extend to greater or fewer chambers of heart 10. In some example, IMD 100 may be equipped with multiple leads that extend to a common chamber of heart, e.g., multiple leads extending to the left ventricle 12. IMD 100 may also be equipped with one or more leads that are placed on the heart through other means providing access to the cardiac tissue, such as surgical epicardial lead placement, and other pericardial access approaches. In some examples, IMD 100 may be equipped with a left ventricular lead that is placed on the heart endocardially. Additionally, although illustrated as implanted on the right side of patient 1 in FIG. 1, IMD 100 may in other examples be implanted on the left side of the pectoral region of the patient, or within the abdomen of the patient.

Electrodes 108, 110, and 112 may attach to portions of heart 10 to provide electrical stimulation or sense the electrical depolarization and repolarization signals of heart 10. Electrode 108, in right ventricle 14, may be affixed to the wall of heart 10 via a screw based mechanism. Electrode 110 may comprise multiple electrodes mounted the same lead, allowing lead 102 to both transmit therapeutic shocks as well as electrical sense data detected by electrode 110. Electrodes 110 and 112 may be attached to the surface of heart 10 via adhesive, barbs, or another permanent or semi-permanent attachment mechanism. Additionally, the heart tissue may be stimulated using other stimulation techniques. For example, an ultrasonic or acoustic wave may be targeted at a specific region of the heart to promulgate a depolarization signal. The pacing device may be an external ultrasound delivery device 101 for applying pacing using an ultrasound wave. The external ultrasound delivery device 101 may include an ultrasound transducer 103 that may be placed outside of the patient's body, on skin, over cardiac tissue (e.g. apex etc.). The ultrasound transducer 103 may provide a high intensity focused ultrasound (HIFU) wave. An example of a configuration in which ultrasonic pacing is delivered to cardiac tissue over the skin may be seen with respect to U.S. patent application Ser. No. 15/009,817 filed Jan. 28, 2016, and assigned to the assignee of the present invention, the disclosure of which is incorporated by reference in its entirety herein.

Figure 2:
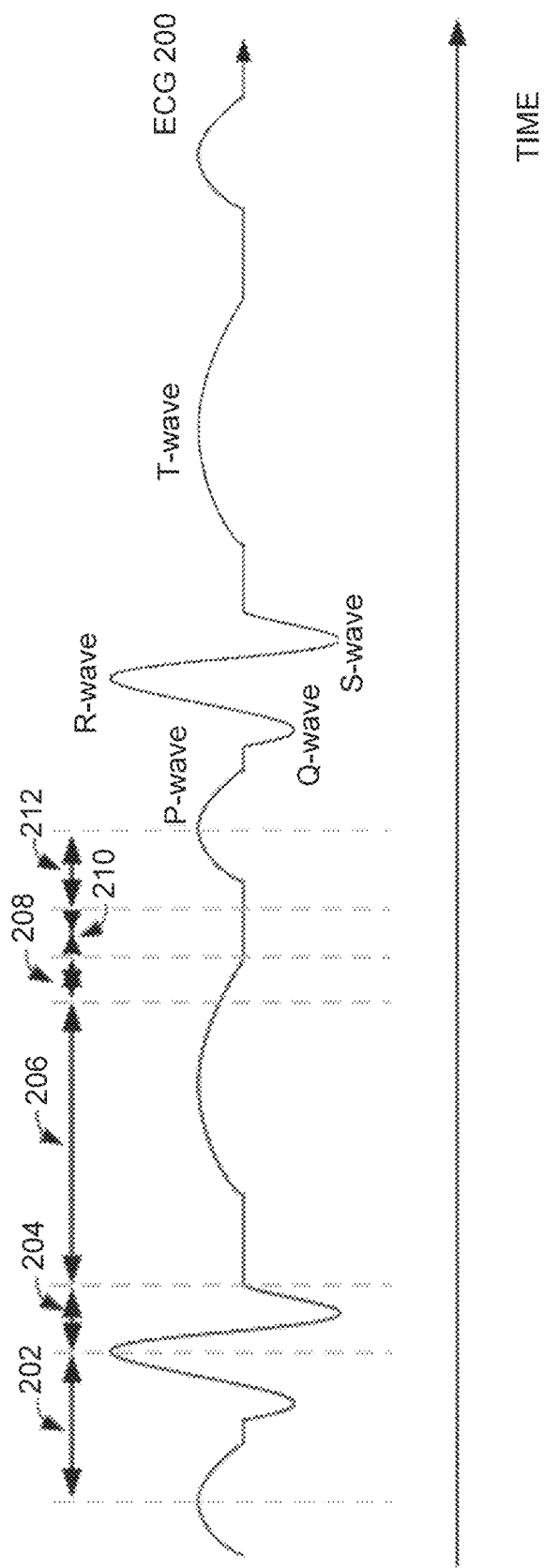
FIG. 2 is a timing diagram showing an example ECG tracing of two healthy heart beats.

FIG. 2 is a timing diagram showing an example ECG tracing 200 in conjunction with certain periods or phases of the mechanical cardiac cycle. The depiction and associated description of FIG. 2 are generalized in the sense that the relationship between the timing of electrical and mechanical events is not necessarily as described for all subjects, or at all times for any given subject.

ECG tracing 200 depicts the electrical signal of two example healthy cardiac cycles. The electrical signal of a healthy heart comprises a series of 5 characteristic waves: the P-wave, Q-wave, R-wave, S-wave, and T-wave. Each of these waves, and the intervals between them, correspond to discrete events in the functioning of a healthy heart.

In general, at some point during period 202, which stretches from the peak of a P-wave to the peak of the subsequent R-wave, atrial systole occurs, which is the contraction of the atria that drives blood from the atria into the ventricles. Period 204, from the peak of the R-wave to the opening of the aortic valve, generally marks a period of isovolumetric contraction. The atrioventricular and aortic valves are closed, preventing blood flow and leading to an increase in pressure in the ventricles but not yet in the aorta. Period 206, bounded by the opening and closing of the aortic valves is generally when ejection occurs during the cardiac cycle. During ejection period 206 the ventricles contract and empty of blood, driving the blood into cardiovascular system. As the contraction of the ventricles complete, the pressure of the blood within the cardiovascular system closes the aortic valves. Period 208, bounded by the closing of the aortic valves and the opening of the atrioventricular valves, is the isovolumetric relaxation of the ventricles. Periods 210 and 212 are collectively known as the late diastole, where the whole heart relaxes and the atria fill with blood. Period 210 corresponds to a rapid inflow of blood while period 212 corresponds to diastasis, the period of slower flow blood into the atria before the atrial systole 202 occurs again.

The P-wave marks the stimulation of the atria and the beginning of the cardiac cycle. The atria contract under the stimulation, forcing blood into the ventricles. The PR segment marks the delay as the depolarization signal travels from the atrioventricular node to the Purkinje fibers. The Q-wave marks the depolarization of the interventricular septum as an initial part of the depolarization of the ventricles. The R-wave follows the Q-wave and represents the depolarization of the ventricles. The S-wave follows the R-wave and represents the later depolarization of the ventricles. The T-wave marks the recovery and repolarization of the ventricles in preparation for the next beat of the heart.

The QRS complex, spanning from the beginning of the Q-wave to the end of the S-wave, represents the electrical activation of the myocardium. Ventricular contraction of both the left and right ventricles is in response to the electrical activation. The QRS complex typically lasts from 80 to 120 ms. The relatively large amplitude of the QRS complex is due to the large muscle mass of the ventricles. Issues affecting the synchrony of the ventricular contraction may be demonstrated in the deformation of the QRS complex. For example, electrical dyssynchrony in the contraction of the ventricles can widen the R-wave or produce two R-wave peaks, typically labeled the r-wave and R'-wave, corresponding to the depolarization of each ventricle. The S-wave and the T-wave may be morphologically different than in an ECG tracing of a healthy heart.

Figure 3:
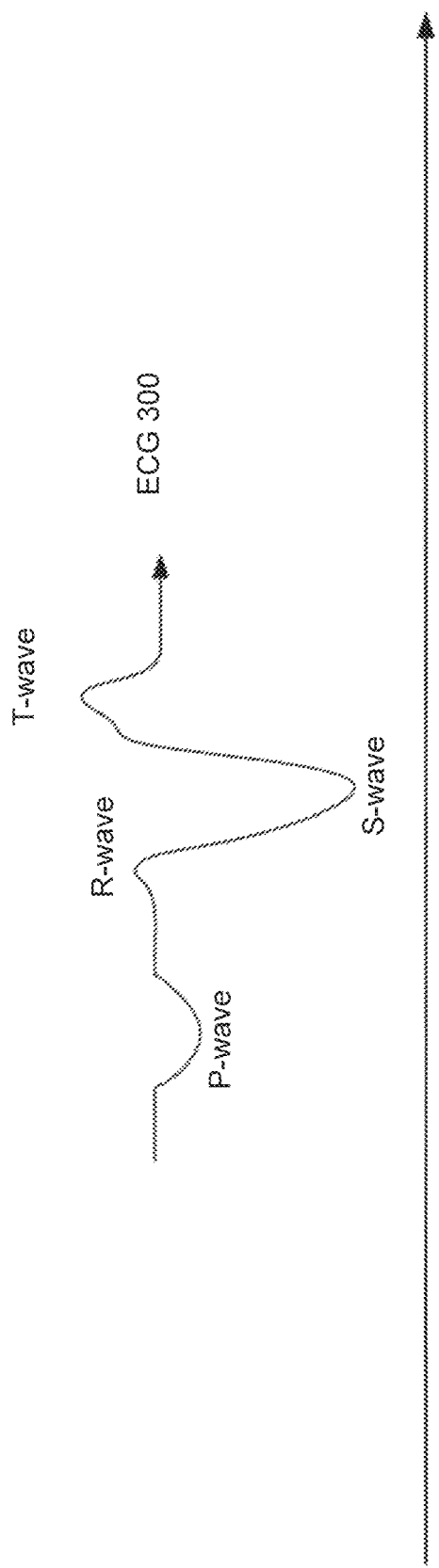
FIG. 3 is a timing diagram showing an example ECG tracing of a patient suffering from left bundle branch block.

FIG. 3 is a timing diagram showing ECG tracing 300. ECG tracing 300 depicts the electrical signal of a patient suffering from a left bundle branch block. A sign of the condition is the presence of an rS complex versus the typical QRS complex, though other variations of Q, R, and S waves form combinations that may be present in patients suffering from a left bundle branch block, right bundle branch blocks, or other ventricular conduction conditions. The extended duration of the rS complex indicates an extended ventricular contraction time, likely due to electrical dyssynchronies.

Diagnosis of a left or right bundle branch block, or cardiac electrical dyssynchrony in general, typically involves measuring the duration of the QRS complex (or other complex marking the depolarization of the ventricles). QRS complexes lasting 100 ms or longer may indicate a partial bundle branch block and 120 ms or longer a complete bundle branch block. In FIG. 3, the initial Q-wave is not visible, instead the tracing shows an initial r-wave, corresponding to the initial depolarization of the right ventricle and followed by an S-wave marking the rapid depolarization of both ventricles after the cardiac signal has reached the left ventricle after traveling through the myocardium of the heart, rather than through the bundle branches. Because the myocardium conducts electricity more slowly than the bundle branches, the entire complex is spread out over a longer period.

Absent a case of bundle branch block—such as the one shown in FIG. 3—or other condition, diagnosis may be more challenging. Thus, occult dyssynchronies may be present that, while responsive to CRT, may not be readily identifiable from an examination of the typical 12-lead ECG. These occult dyssynchronies may manifest in the electrical signals generated by the heart and measured on the surface of the torso and may be diagnosable through alternative means of analysis, such as by determining cardiac activation times at a plurality of spatially distributed locations according to the techniques described herein.

Figure 4A:
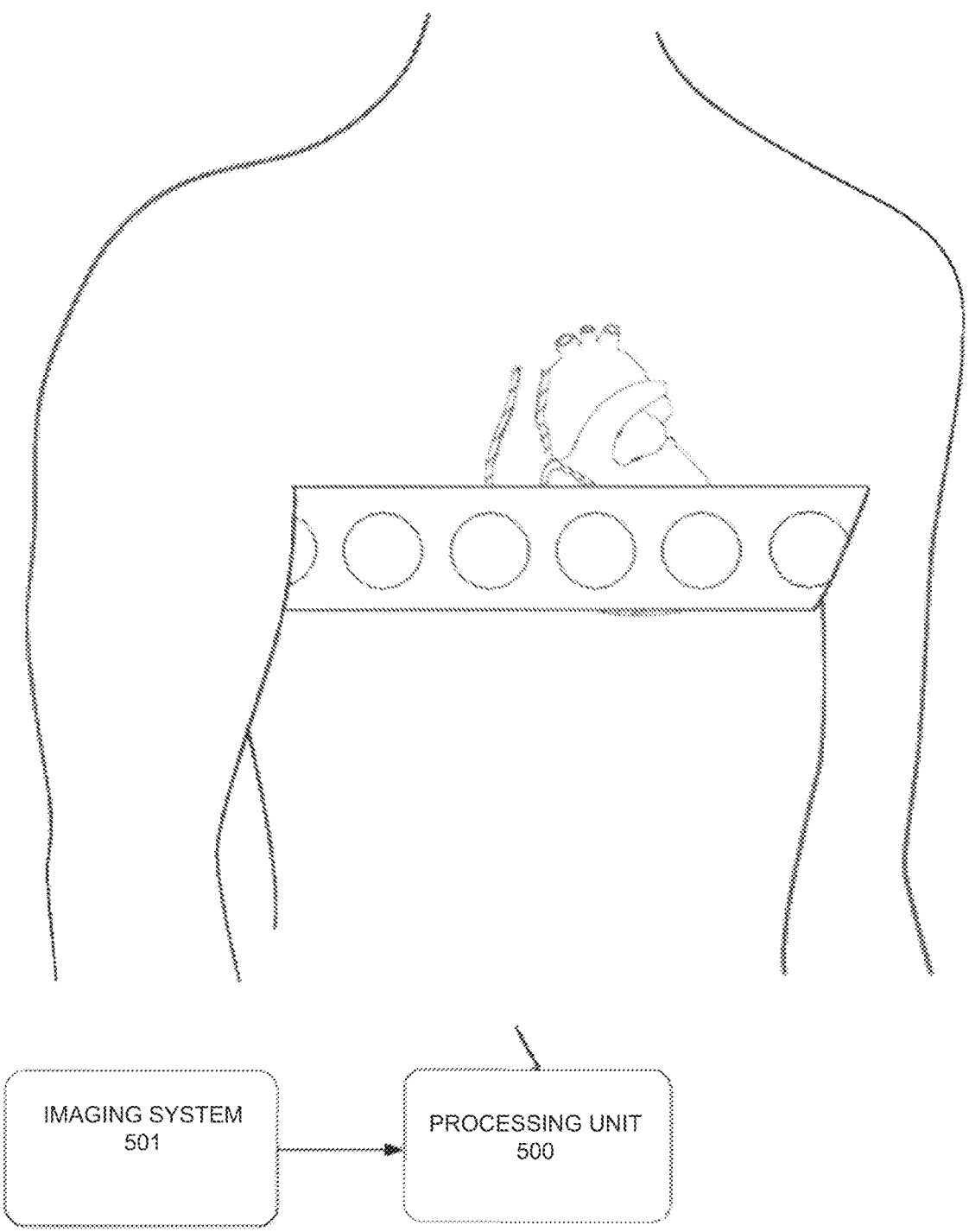
FIGS. 4A and 4B are conceptual diagrams illustrating example systems for measuring torso-surface potentials.
Figure 4B:
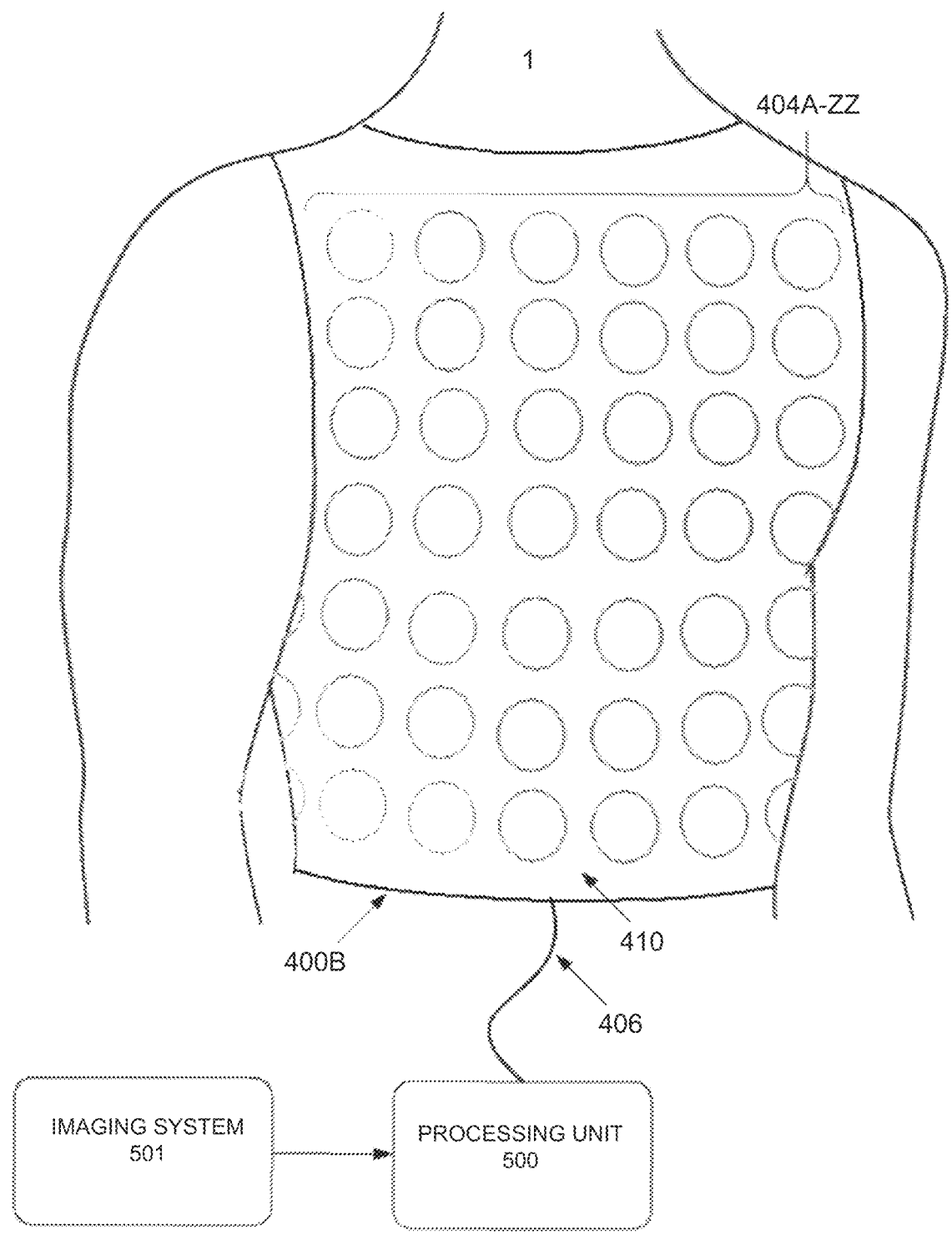

FIGS. 4A and 4B are conceptual diagrams illustrating example systems for measuring body-surface potentials and, more particularly, torso-surface potentials. In one example illustrated in FIG. 4A, sensing device 400A, comprising a set of electrodes 404A-F (generically "electrodes 404") and strap 408, is wrapped around the torso of patient 1 such that the electrodes surround heart 10. As illustrated in FIG. 4A, electrodes 404 may be positioned around the circumference of patient 1, including the posterior, lateral, and anterior surfaces of the torso of patient 1. In other examples, electrodes 404 may be positioned on any one or more of the posterior, lateral, and anterior surfaces of the torso. Electrodes 404 may be electrically connected to processing unit 500 via wired connection 406. Some configurations may use a wireless connection to transmit the signals sensed by electrodes 404 to processing unit 500, e.g., as channels of data.

Although in the example of FIG. 4A sensing device 400A comprises strap 408, in other examples any of a variety of mechanisms, e.g., tape or adhesives, may be employed to aid in the spacing and placement of electrodes 404. In some examples, strap 408 may comprise an elastic band, strip of tape, or cloth. In some examples, electrodes 404 may be placed individually on the torso of patient 1.

Electrodes 404 may surround heart 10 of patient 1 and record the electrical signals associated with the depolarization and repolarization of heart 10 after the signals have propagated through the torso of patient 1. Each of electrodes 404 may be used in a unipolar configuration to sense the torso-surface potentials that reflect the cardiac signals. Processing unit 500 may also be coupled to a return or indifferent electrode (not shown) which may be used in combination with each of electrodes 404 for unipolar sensing. In some examples, there may be 12 to 16 electrodes 404 spatially distributed around the torso of patient 1. In other examples, there may be more than 40 electrodes 404 distributed around the torso of patient 1. Other configurations may have more or fewer electrodes 404.

Processing unit 500 may record and analyze the torso-surface potential signals sensed by electrodes 404. As described herein, processing unit 500 may be configured to provide an output to a user indicating the electrical dyssynchrony in heart 10 of patient 1. The user may make a diagnosis, prescribe CRT, position therapy devices, e.g., leads, or adjust or select treatment parameters based on the indicated electrical dyssynchrony.

In some examples, the analysis of the torso-surface potential signals by processing unit 500 may take into consideration the location of electrodes 404 on the surface of the torso of patient 1. In such examples, processing unit 500 may be communicatively coupled to an imaging system 501, which may provide an image that allows processing unit 500 to determine coordinate locations of each of electrodes 404 on the surface of patient 1. Electrodes 404 may be visible, or made transparent through the inclusion or removal of certain materials or elements, in the image provided by imaging system 501.

FIG. 4B illustrates an example configuration of a system that may be used to evaluate electrical dyssynchrony in heart 10 of patient 1. The system comprises a sensing device 400B, which may comprise vest 410 and electrodes 404 A-ZZ (generically "electrodes 404"), a processing unit 500, and imaging system 501. Processing unit 500 and imaging system 501 may perform substantially as described above with respect to FIG. 4A. As illustrated in FIG. 4B, electrodes 404 are distributed over the torso of patient 1, including the anterior, lateral, and posterior surfaces of the torso of patient 1.

Sensing device 400B may comprise a fabric vest 410 with electrodes 404 attached to the fabric. Sensing device 400B may maintain the position and spacing of electrodes 404 on the torso of patient 1. Sensing device 400B may be marked to assist in determining the location of electrodes 404 on the surface of the torso of patient 1. In some examples, there may be 150 to 256 electrodes 404 distributed around the torso of patient 1 using sensing device 400B, though other configurations may have more or fewer electrodes 404.

Figure 5:
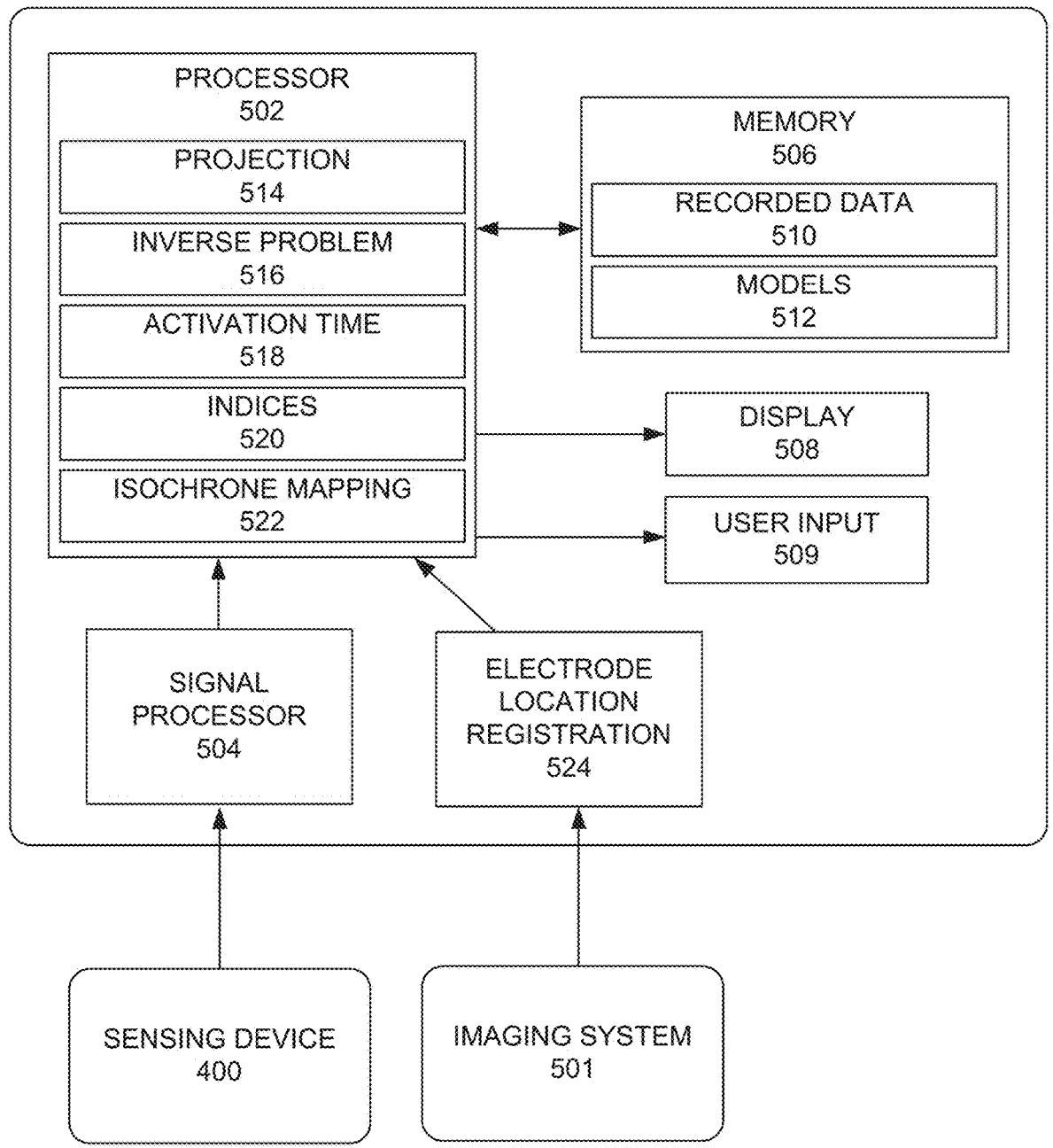
FIG. 5 is a block diagram illustrating an example system for measuring torso-surface potentials.

FIG. 5 is a block diagram illustrating an example system for measuring torso-surface potentials and providing indications of electrical dyssynchrony. The example system may comprise a processing unit 500 and a set of electrodes 404 on a sensing device 400, e.g., one of example sensing devices 400A or 400B (FIGS. 4A and 4B). The system may also include an imaging system 501.

As illustrated in FIG. 5, processing unit 500 may comprise a processor 502, signal processor 504, memory 506, display 508, and user input device 509. Processing unit 500 may also include an electrode location registration module 524.

In the illustrated example, processor 502 comprises a number of modules and, more particularly, a projection module 514, an inverse problem module 516, an activation time module 518, an indices module 520, and an isochrones mapping module 522. Memory 506 may store recorded data 510 and models 512.

Processing unit 500 may comprise one or more computing devices, which may be co-located, or dispersed at various locations. The various modules of processing unit 500, e.g., processor 502, projection module 514, inverse problem module 516, activation time module 518, statistics module 520, isochrones mapping module 522, signal processor 504, electrode location registration module 524, display 508, memory 506, recorded data 510 and torso models 512 may be implemented in one or more computing devices, which may be co-located, or dispersed at various locations. Processor 502, and the modules of processor 502, may be implemented in one or more processors, e.g., microprocessors, of one or more computing devices, as software modules executed by the processor(s). Electrode location registration module 524 may, in some examples, be implemented in imaging system 501.

In addition to the various data described herein, memory 506 may comprise program instructions that, when executed by a programmable processor, e.g., processor 502, cause the processor and any components thereof to provide the functionality attributed to a processor and processing unit herein. Memory 506 may include any volatile, non-volatile, magnetic, optical, or electrical media, such as a hard disk, magnetic tape, random access memory (RAM), read-only memory (ROM), CD-ROM, non-volatile RAM (NVRAM), electrically-erasable programmable ROM (EEPROM), flash memory, or any other digital or analog media. Memory 506 may comprise one or more co-located or distributed memories. Memory 506 may comprise a tangible article that acts as a non-transitory storage medium for data and program instructions.

The torso-surface potential signals sensed by electrodes 404 of sensing device 400 may be received by signal processor 504 of processing unit 500. Signal processor 504 may include an analog-to-digital converter to digitize the torso-surface potential signals. Signal processor 504 may also include various other components to filter or otherwise condition the digital signals for receipt by processor 502.

Electrode location registration module 524 may receive imaging data from imaging system 501. Electrode location registration module 524 analyzes the imaging data. In particular, electrode registration location module 524 identifies electrodes 404, or elements co-located with the electrodes that are more clearly visible via the imaging modality, within the images. Electrode location registration module 524 may further identify the locations of each of the electrodes on the surface of the patient and/or within a three-dimensional coordinate system. In some examples, the locations of electrodes 404 may be manually identified and registered with processing unit 500, e.g., by a user, via electrode registration module 524.

The imaging data may comprise data representing one or more images of patient 1 wearing electrodes 404, e.g., of a sensing device 400. In some examples, the images may be obtained before or during a medical procedure, e.g., a surgical procedure to implant a cardiac rhythm device and lead system for delivery of CRT.

In some examples, processor 502 may store the torso-surface potential signals, imaging data from imaging system, electrode location data from electrode location registration module, or any values disclosed herein that are derived by processing of such signals and data by processor 502, within memory 506 as recorded data 510. Each recorded torso-surface potential signal, or other values derived therefrom, may be associated with a location of the electrode 404 that sensed the torso-surface potential signal. In this manner, the torso-surface potential data may be correlated with the position of electrodes 404 on the torso of patient 1, or within a three-dimensional coordinate system, enabling spatial mapping of the data to particular locations on the surface of the torso or within the coordinate system. In some examples, aspects of the techniques described herein may be performed at some time after the acquisition of the torso-surface potential signals and location data based on recorded data 510.

Processor 502 may be configured to provide one or more indications of electrical dyssynchrony based on the torso-surface potential signals and, in some examples, the electrode location data. Example indications of electrical dyssynchrony include indices illustrating activation times for each electrode/location distributed about the torso or heart, or for one or more subsets of electrodes located within a common region, e.g., within a left posterior, left anterior, right posterior, or right anterior region. In some examples, processor 502 may be configured to provide a set of two or more different indications, e.g., several different indications, for each of two or more different regions, e.g., several different regions, of the torso or heart.

Some indications of dyssynchrony may include statistical values or other indices derived from activation times for each electrode location or one or more subsets of electrodes within one or more regions. Other examples indications of electrical dyssynchrony that may be determined based on activation times at various electrodes/locations include graphical indications, such as an isochrone or other activation maps, or an animation of electrical activation. Other examples indications of electrical dyssynchrony that may be determined based on activation times at various electrodes/locations include identifying one of a predetermined number of dyssynchrony levels, e.g., high, medium, or low, via text or color, e.g., red, yellow, green, for example.

In some examples, the various indications of dyssynchrony for one or more regions may be determined based on data collected at two or more different times and/or under two or more different conditions. For example, the various indications of dyssynchrony may be determined based on torso-potential signals collected during intrinsic conduction of heart 10, and also determined based on torso-potential signals collected during CRT. In this manner, the potential dyssynchrony-reducing benefit of CRT may be evaluated for the patient by comparing the different values, graphical representations, or the like, resulting from intrinsic conduction and CRT. A short pacing signal reduces the potential for interference from the intrinsic or natural pacing of the heart. As another example, the various indications of dyssynchrony may be determined each of a plurality of different times based on torso-potential signals collected during delivery of CRT with different lead positions, electrode configurations, or CRT parameters, e.g., A-V or V-V interval values. In this manner, the relative dyssynchrony-reducing benefits of the different lead positions, electrode configurations, or CRT parameters positions may be evaluated for the patient by comparing the different values, graphical representations, or the like.

Models 512 may include a plurality of different models, e.g., three-dimensional models, of the human torso and heart. A model torso or model heart may be constructed by manual or semi-automatic image segmentation from available databases of previously acquired medical images (CT/MRI) of a plurality of subjects, e.g., cardiomyopathy patients, different than patient 1, using commercially available software. Each model may be discretized using a boundary element method. A plurality of different torso models may be generated. The different models may represent different subject characteristics, such as different genders, disease states, physical characteristics (e.g., large frame, medium frame and small frame), and heart sizes (e.g., x-large, large, medium, small). By providing input via user input 509, a user may select from among the various model torsos and model hearts that may be stored as models 512 in memory 506, so that the user may more closely match the actual torso and heart 10 of patient 1 with the dimensions and geometry of a model torso and model heart. In some examples, medical images of the patient, e.g., CT or MRI images, may be manually or semi-automatically segmented, registered, and compared to models 512 for selection from amongst the models 512. Furthermore, single or multiple view 2-D medical images (e.g., x-ray, fluoroscopy) may be segmented or measured to determine approximate heart and torso dimensions specific to the patient in order to select the best fit model torso and heart.

Projection module 514 may project the locations of electrodes 404, e.g., stored as recorded data 510 within of memory 506, onto an appropriate, e.g., user-selected, model torso contained in model data module 512 of memory 506. By projecting the location of electrodes 404 onto the model torso, projection module 514 may also project the torso-surface potential signals of patient 1 sensed by electrodes 404 onto the model torso. In other examples, the measured electrical potentials may be interpolated and resampled at electrode positions given by the model. In some examples, projecting the torso-surface potentials onto the model torso may allow processor 502, via inverse problem module 516, to estimate the electrical activity of at various locations or regions of the model heart corresponding to heart 10 of patient 1 that produced the measured torso-surface potentials.

Inverse problem module 516 may be configured to solve the inverse problem of electrocardiography based on the projection of the measured torso-surface potentials, recorded by electrodes 404, onto the model torso. Solving the inverse problem of electrocardiography may involve the estimation of potentials or activation times in heart 10 based on a relationship between the torso and heart potentials. In one example method, model epicardial potentials are computed from model torso potentials assuming a source-less volume conductor between the model heart and the model torso in an inverse Cauchy problem for Laplace's equation. In another example method, an analytic relationship between torso-surface potentials and the cardiac transmembrane potential is assumed. Torso-surface potentials may be simulated based on this relationship. In some examples, inverse problem module 516 may utilize techniques described by Ghosh et al. in "Accuracy of Quadratic Versus Linear Interpolation in Non-Invasive Electrocardiographic Imaging (ECGI)," Annals of Biomedical Engineering, Vol. 33, No. 9, September 2005, or in "Application of the L1-Norm Regularization to Epicardial Potential Solution of the Inverse Electrocardiography Problem," Annals of Biomedical Engineering, Vol. 37, No. 5, 2009, both of which are incorporated herein by reference in their entireties. In other examples, any known techniques for solving the inverse problem of electrocardiography may be employed by inverse problem module 516.

Activation time module 518 may compute the activation times directly from measured torso-surface potentials, or by estimating model transmembrane potentials. In either case, an activation time for each electrode/location may be determined as a time period between two events, such as between the QRS complex onset and the minimum derivative (or steepest negative slope) of the sensed torso potential signal or estimate epicardial potential signal. Thus, in one example, cardiac activation times are estimated from the steepest negative slope of the model epicardial electrograms. Cardiac activation times (parameters in the analytic relationship between torso-surface potential and cardiac transmembrane potential) may, in other configurations, be computed based on minimizing the least square difference between the measured torso-surface potentials and simulated torso-surface potentials. A color-coded isochrone map of ventricular, epicardial, or torso-surface activation times may be shown by display 308. In other examples, display 308 may show a two-color animation of propagation of the activation wavefront across the surface of the model heart or the torso-surface.

Indices module 520 may be configured to compute one or more indices of electrical dyssynchrony from the torso-surface or cardiac activation times. These indices may aid in the determination of whether the patient is a candidate for CRT, placement of CRT leads, and selection of CRT parameters. For example, LV lead 102 (FIG. 1) may be positioned at the site that reduces dyssynchrony from one or more indices or, alternatively, the largest electrical resynchronization as demonstrated by the indices. The same indices may be also used for programming A-V and/or V-V delays during follow-up. As indicated above, the indices may be determined based on the activation times for all electrodes/locations, or for one or more subsets of electrodes in one or more regions, e.g., to facilitate comparison or isolation of a region, such as the posterior and/or left anterior, or left ventricular region.

One of the indices of electrical dyssynchrony may be a standard deviation index computed as the standard deviation of the activations-times (SDAT) of some or all of electrodes 404 on the surface of the torso of patient 1. In some examples, the SDAT may be calculated using the estimated cardiac activation times over the surface of a model heart.

A second example index of electrical dyssynchrony is a range of activation times (RAT) which may be computed as the difference between the maximum and the minimum torso-surface or cardiac activation times, e.g., overall, or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart 10 have been delayed in activation. In some examples, the RAT may be calculated using the estimated cardiac activation times over the surface of a model heart.

A third example index of electrical dyssynchrony estimates the percentage of electrodes 404 located within a particular region of interest for the torso or heart, whose associated activation times are greater than a certain percentile, for example the 70th percentile, of measured QRS complex duration or the determined activation times for electrodes 404. The region of interest may be a posterior, left anterior, and/or left-ventricular region, as examples. This index, the percentage of late activation (PLAT), provides an estimate of percentage of the region of interest, e.g., posterior and left-anterior area associated with the left ventricular area of heart 10, which activates late. A large value for PLAT may imply delayed activation of substantial portion of the region, e.g., the left ventricle 12 (FIG. 1), and the potential benefit of electrical resynchronization through CRT by pre-exciting the late region, e.g., of left ventricle 12. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

Isochrone mapping module 522 may be configured to generate an isochrone map depicting the dispersion of activation times over the surface of the torso of patient 1 or a model heart. Isochrone mapping module 522 may incorporate changes in the torso-surface or cardiac activation times in near real-time, which may permit near instant feedback as a user adjusts a CRT device or monitors patient 1 to determine if CRT is appropriate. Isochrone maps generated by isochrone mapping module 522 may be presented to the user via display 508.

In general, processor 502 may generate a variety of images or signals for display to a user via display 508 based on the measured torso-surface potentials, calculated torso-surface or estimated cardiac activation times, or the degree of change in electrical dyssynchrony. For example, a graded response reflecting the efficacy of a particular location of the LV lead 102 during biventricular pacing or single ventricle fusion pacing may be provided to the physician in terms of a red, yellow and green signal. A red signal may be shown if the reduction in electrical dyssynchrony during CRT pacing compared to intrinsic rhythm is negative (an increase in electrical dyssynchrony) or minimal, e.g., less than 5%. A yellow signal may be triggered if there is some reduction in electrical dyssynchrony during CRT pacing compared to intrinsic rhythm, for example between 5% and 15%, but there may be potentially better sites for lead placement. If the reduction in electrical dyssynchrony during CRT pacing compared to intrinsic rhythm is substantial, e.g., greater than 15%, a green signal may be triggered indicating to the physician that the present site provides effective changes in synchronization. The feedback from this system in combination with other criteria (like magnitude of pacing threshold, impedance, battery life, phrenic nerve stimulation) may be also used to choose an optimal pacing vector for one or more multipolar leads. The feedback from this system may be also used for selecting optimal device timings (A-V delay, V-V delay, etc) influencing the extent of fusion of intrinsic activation with paced activation from single or multiple ventricular sites, or discerning acute benefit of single site fusion pacing versus multi-site pacing and choice of appropriate pacing type.

Display 508 may also display three-dimensional maps of electrical activity over the surface of the torso of patient 1 or over a model heart. These maps may be isochrone maps showing regions of synchronous electrical activity as the depolarization progresses through heart 10 of patient 1. Such information may be useful to a practitioner in diagnosing asynchronous electrical activity and developing an appropriate treatment, as well as evaluating the effectiveness of the treatment.

Figure 6:
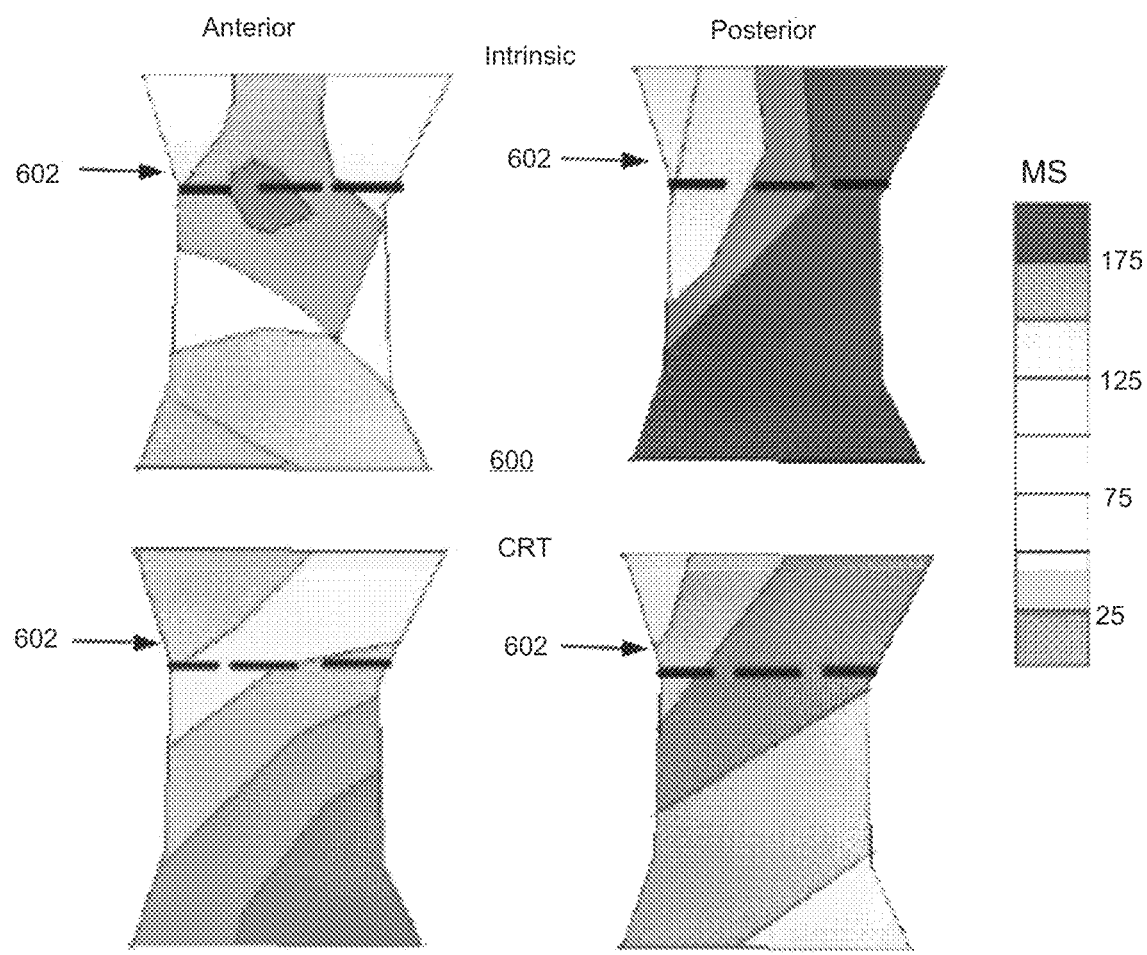
FIG. 6 is a series of simulated isochrone maps of torso-surface activation times for typical left bundle branch block intrinsic rhythm and CRT pacing.

FIG. 6 is a series of simulated isochrone maps 600 of torso-surface activation times over the torso of a patient suffering from an electrical dyssynchrony in the left ventricle before and during treatment with a CRT device. The isochrone maps before (intrinsic) and after treatment are divided into two views: anterior and posterior. Line 602 represents the location of a subset of electrodes 404, e.g., a subset of electrodes 404 of sensing device 400B, that may be used to calculate one or more indices of electrical dyssynchrony. In some examples, line 602 may represent electrodes 404 on sensing device 400A.

The isochrone maps 600 of the natural and CRT assisted torso-surface activation times may be generated using multiple electrodes 404 distributed over the surface of the torso of a patient, e.g., using sensing device 400B. Generation of the isochrone maps 600 may include determining the location of electrodes 404, and sensing torso-surface potential signals with the electrodes. Generation of the isochrone maps 600 may further include calculating the torso-surface activation time for each electrode or electrode location by determining the point in the recorded QRS complex of the signal sensed by the electrodes corresponding to the maximum negative slope. In other examples, the torso-surface activation times may be determined by identifying the minimum derivative of the QRS complex. The measured torso-surface activation times may then be standardized and an isochrone map of the surface of the torso of the patient generated.

The delayed activation of certain locations associated with certain ones of electrodes 404 due to the electrical dyssynchrony is apparent in the posterior views of the intrinsic torso-surface activation times. Regions 604 indicate increased delay in the activation of the underlying heart. The corresponding posterior view during treatment with a CRT device indicate that regions 606, the same location as regions 604 on the maps of intrinsic torso-surface activation times, exhibits increased synchrony in electrical ventricular activity. The CRT maps exhibit decreased range and a lower standard deviation of torso-surface activation times. Further, the posterior regions no longer exhibit delayed activation times. The isochrone map of the torso-surface activation times during intrinsic and CRT pacing and changes in distribution of activation-times from intrinsic to CRT pacing may be used for diagnostic purposes or the adjustment of a CRT device.

One or more indices of electrical dyssynchrony may also be calculated from the torso-surface activation times used to generate isochrone maps 600. For example, SDAT, an indication of the spread of the activation times, for the patient's intrinsic heart rhythm using the complete set of electrodes 404 is 64. Using the reduced lead set marked by line 602 results in an SDAT of 62. The RAT for the intrinsic heart rhythm and complete lead set is 166.5 while the reduced lead set has a RAT of 160. PLAT for the intrinsic heart rhythm using the reduced and complete lead sets are 56.15% and 66.67%, respectively. This indicates that using a reduced lead set that circumscribes the heart of the patient, e.g., sensing device 400A and associated electrodes 404, may provide comparable indices of electrical dyssynchrony compared to using an electrode set covering the torso of the patient, such as sensing device 400B.

The indices of electrical dyssynchrony also provide indication of the effectiveness of the CRT device, with the SDAT for the reduced set of electrodes declining to 24, the RAT to 70 and PLAT to 36%. This indicates that the torso-surface activation times during CRT treatment were more narrowly distributed and in a smaller range than in the normal heart rhythm and that the percentage of electrodes 404 located on the left anterior surface of the torso of the patient registering late activation times decreased markedly.

Figure 7:
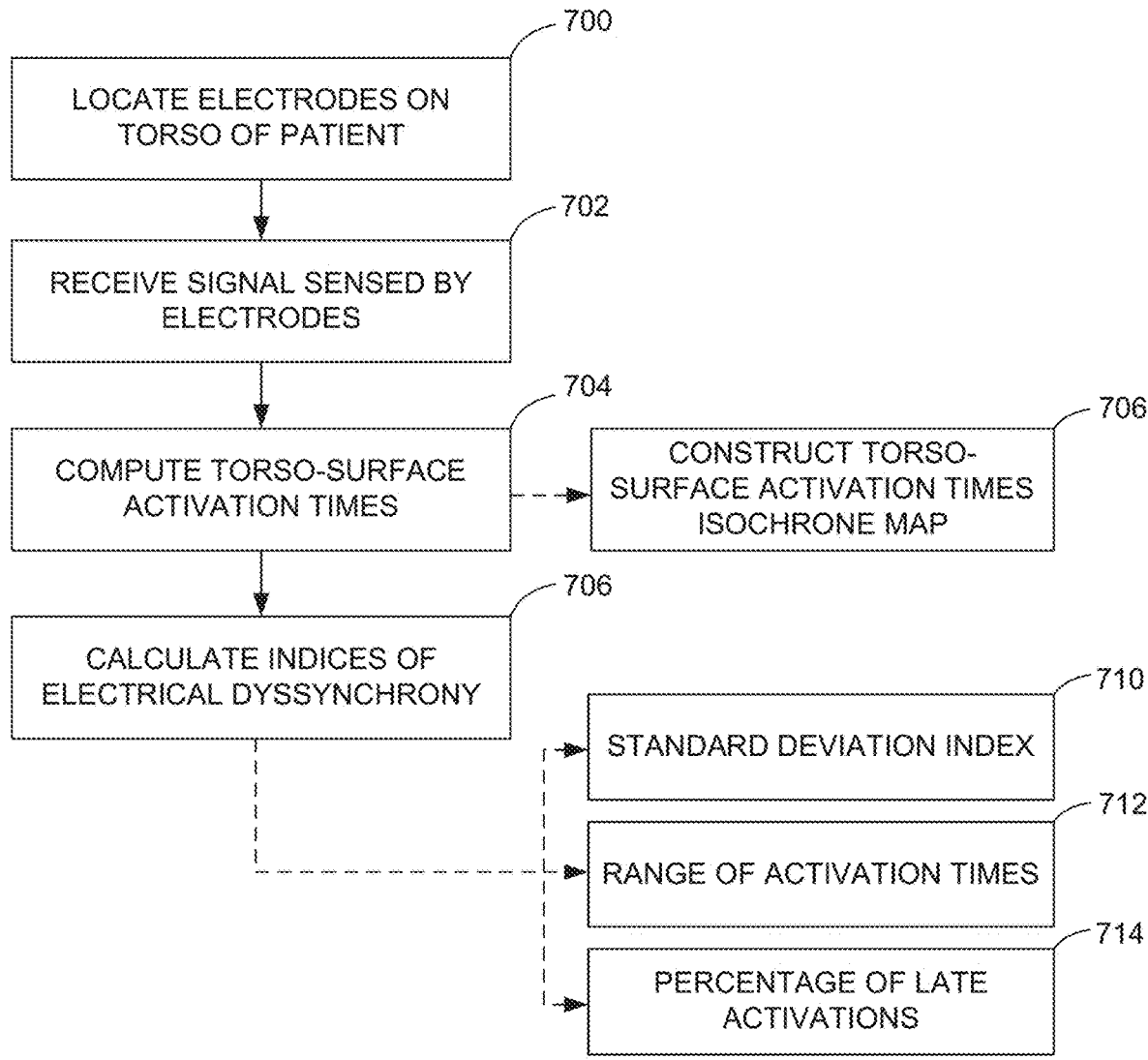
FIG. 7 is a flow diagram illustrating an example operation of a system to provide indications of the cardiac electrical dyssynchrony of a patient based on torso-surface activation times.

FIG. 7 is a flow diagram illustrating an example operation of a system to evaluate the cardiac electrical dyssynchrony of a patient via the torso-surface activation times. The location of electrodes, e.g., electrodes 404 (FIGS. 4A and 4B), distributed over the surface of the torso of the patient may be determined (700). A cardiac event, e.g., a depolarization, may generate an electrical signal that propagates through the torso of a patient, e.g., patient 1 (FIG. 1) and registers on the electrodes. The signal sensed by the electrodes may be received (702), e.g., by processing unit 500 (FIG. 5). The processing unit may calculate the torso-surface activation times (704). In some examples, the processing unit may also construct a torso-surface activation times isochrone map (706). The processing unit may also calculate at least one index of cardiac electrical dyssynchrony (708). These indices may comprise one or more of the SDAT (710), RAT (712), and the PLAT (714).

A cardiac event, such as a depolarization, generates an electrical signal that propagates through the torso. The electrical signal may comprise a QRS complex, or a variant caused by a heart related condition such as a left or right bundle branch block. The electrical signal may not propagate uniformly through the torso of a patient due to variations in conductivity within the torso and the heart. These delays may manifest in electrodes distributed over the surface of the torso of the patient registering the same electrical signal at different points in time.

The electrical signal generated by the cardiac event may register on the plurality of electrodes distributed over the surface of the torso of patient. The electrodes may be distributed over the anterior, lateral, and/or posterior surfaces of the torso, allowing the generation of a three-dimensional picture of the electrical activity occurring within the torso. In some examples, the electrodes may be placed to provide extensive coverage both above and below the heart, e.g., by using sensing device 400B (FIG. 4B). In other examples, a reduced set of electrodes may be arranged around the circumference of the torso, circumscribing the heart of the patient, e.g., using sensing device 400A (FIG. 4A). The electrodes may receive the complete waveform of the electrical signal generated by the cardiac event, and transmit the signal to a processing unit.

The location of electrodes distributed over the surface of the torso of the patient may be determined (700). Locating the electrodes may be performed automatically, e.g. by imaging system 501 and electrode location registration module 524 of processing unit 500 (FIG. 5). The electrodes may be located by analyzing one or more images of the torso of a patient and performing a pattern matching routine, e.g., recognizing the shape of an electrode against the torso of the patient, and storing the location of the electrode on the torso of the patient in processing unit memory. In other examples, the location of sensing device 400A or 400B may be determined and the locations of the electrodes determined based on the position of the sensing device, e.g., basing the position of the electrode on the patient through the known position of the electrode on the sensing device. In another example, the position of the electrodes may be measured manually.

The processing unit may receive the electrical signal from the electrodes and record the output in memory (702). The processing unit may record the raw output, e.g., the raw ECG tracing from each electrode, as well as location data for the electrodes, allowing the electrical signals detected by the electrodes to be mapped onto the surface of the torso of the patient.

The processing unit may compute the torso-surface activation times (704). A processor, e.g., processor 502 of processing unit 500 (FIG. 5), may retrieve ECG tracing data stored within the processing unit memory and analyze the tracing to detect depolarization of the ventricles of the heart, typically marked by a QRS complex in the tracing. The processor may, in some examples, detect ventricular depolarization by determining the time of the minimum derivative (or steepest negative slope) within the QRS complex measured with respect to the time of QRS complex onset. The determination of the activation time may be made for each electrode and stored in the processing unit memory.

In some configurations, the processing unit may construct an isochrone map of the torso-surface activation times, allowing the user to visually inspect the propagation of the electrical signals of the heart after progression through the torso of the patient. The isochrone map may be constructed by dividing the range of measured torso-surface activation times into a series of sub-ranges. The location of each electrode on the surface of the torso of the patient may be graphically represented. Regions of electrodes whose measured activation times fall within the same sub-range may be represented by the same color on the graphical representation.

The processing unit may also calculate one or more indices of electrical dyssynchrony based on the torso-surface activation times (708). These indices may include the SDAT (710), RAT (712), and PLAT (714). In some examples, the PLAT may be determined as the percentage of posterior electrodes activating after a certain percentage of the QRS complex duration.

As discussed above, in some examples, the construction of a torso-surface activation times isochrone map (706), or other graphical representation of dyssynchrony, as well as the calculation of indices of electrical dyssynchrony (708), may be performed for a particular region of the torso based the signals received from electrodes (702) in such regions. Graphical representations and indices of electrical dyssynchrony may be determined for each of a plurality of regions based on the signals received from the electrodes for such regions. In some examples, the representations and indices for various regions may be presented together or compared.

Figure 8:
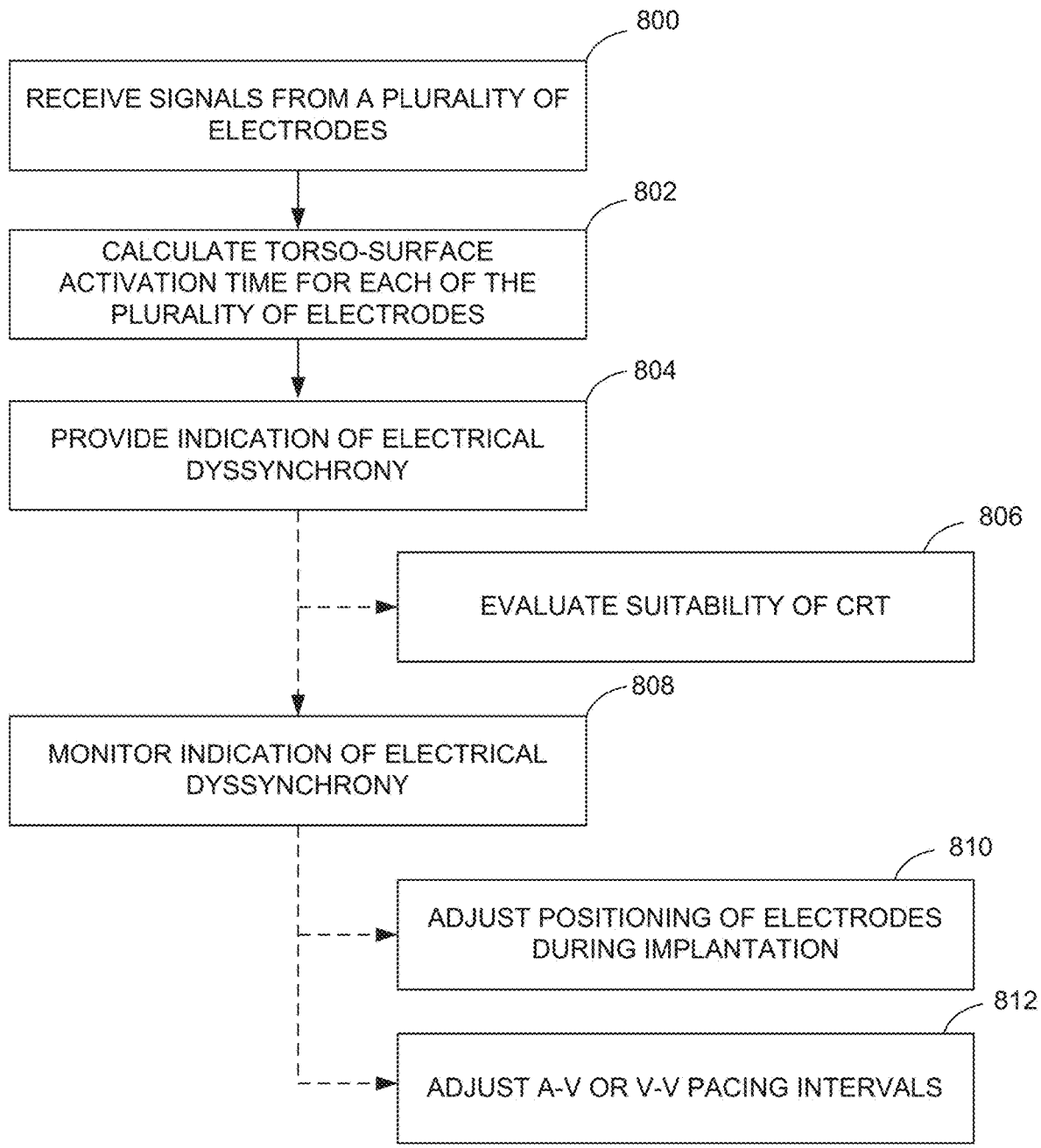
FIG. 8 is a flow diagram illustrating an example technique for prescribing and configuring CRT based on an assessment cardiac electrical dyssynchrony of a patient via the torso-surface activation times.

FIG. 8 is a flow diagram illustrating an example technique for measuring the cardiac electrical dyssynchrony of a patient via measured torso-surface activation times. A processing unit 500 may receive torso-surface potential signals from a plurality of electrodes (800), e.g., electrodes 404 (FIGS. 4A and 4B). The processing unit 500 may calculate the torso-surface activation times for each of the plurality of electrodes (802). The processing unit 500 may provide at least one indication of cardiac electrical dyssynchrony (804).

A user may evaluate the whether a patient is a candidate for CRT based on the at least one indication of electrical dyssynchrony (806). The user may also monitor the at least one indication of electrical dyssynchrony (808), and use the changes in the at least one indication to aid in adjusting the positioning of electrodes, e.g., electrodes 108, 110, and 112 (FIG. 1), during implantation of a CRT device (810), e.g., IMD 100 (FIG. 1), or selection of the various programmable parameters, such as electrode combination and the A-V or V-V pacing intervals, of the CRT device (812), during implantation or a follow-up visit.

The various indications of cardiac electrical dyssynchrony described herein, such as statistical or other indices, or graphical representations of activation times, may indicate the presence of damage to electrical conductivity of the heart of the patient, for example the presence of a left or right bundle branch block, that may not be apparent from the examination of a standard 12-lead ECG readout. For example, a large SDAT indicates that the activation of the ventricles is occurring over a large time span, indicating that the depolarization of the ventricles is not occurring simultaneously. A large RAT also indicates a broad range of activation times and asynchronous contraction of the ventricles. A high PLAT indicates that a specific region of the heart, e.g., the posterior regions associated with the left ventricle, may be failing to activate in concert with the measured QRS complex. Additionally, by monitoring the at least one indication of cardiac electrical dyssynchrony, the user may detect changes in the electrical activity of the heart caused by different treatments or treatment configurations.

As described above, the various indications of electrical dyssynchrony, such as statistical indexes, may be calculated for each of a plurality of regions, e.g., posterior, left anterior, or the like, based on torso-surface activations times from the region. Additionally, evaluating whether a patient is a candidate for CRT based on the at least one indication of electrical dyssynchrony (806) may include determining the one or more indications of electrical dyssynchrony based on torso-surface activation times both during intrinsic conduction of the heart, and during CRT. Differences between the indications during intrinsic conduction and CRT may indicate that CRT would provide benefit for the patient, e.g., that the patient is a candidate for CRT. As described above, the user may also evaluate whether a patient is a candidate for CRT based on at least one indication of electrical dyssynchrony based on intrinsic rhythm alone. Furthermore, monitoring the at least one indication of electrical dyssynchrony (808) during implantation or a follow-up visit may include determining the one or more indications of electrical dyssynchrony for each of a plurality of lead positions, electrode configurations, or other parameter values based on torso-surface activation times resulting from delivery of CRT at the positions, or with the electrode configurations or parameter values. In this manner, differences between dyssynchrony indications associated with various locations, electrode configurations, or parameter values may be compared to determine preferred locations, configurations, or values.

Right ventricular (RV) pacing is less common than left ventricular (LV) pacing for resynchronization patients. RV only pacing may cause arrhythmogenic effects in patients. Additionally RV failure is less common in patients than LV failure. However, patients with right heart conduction delays, such as right bundle blockage, may benefit from RV only pacing. Before administering RV only pacing, a patient's unique situation should be analyzed. Analyzing the function of the right ventricle may be difficult using traditional QRS techniques. Because the left ventricle is larger, the electrical signals from the depolarization of the left ventricle may obscure signals from the depolarization of the right ventricle.

Figure 12:
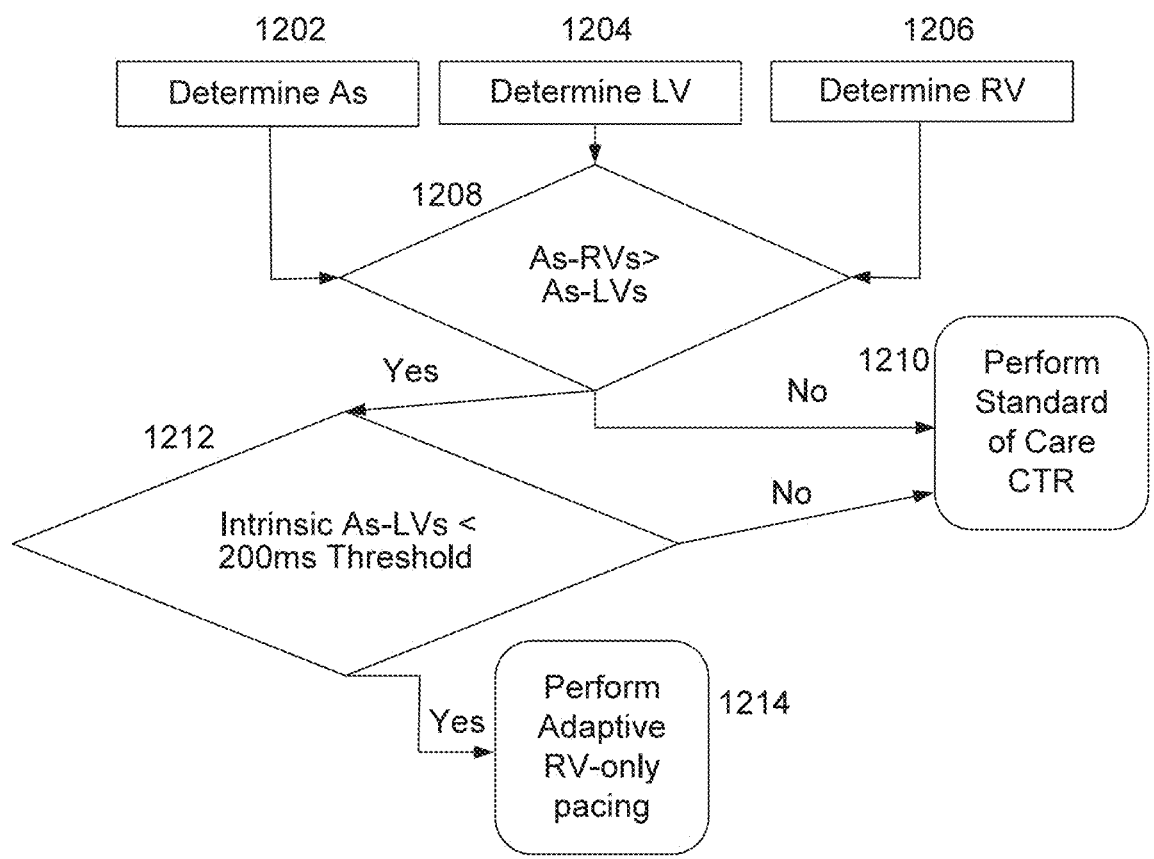
FIG. 12 is a flow diagram illustrating a technique for determining whether a patient is a good candidate for right ventricle only pacing according to some embodiments of the present invention.

FIG. 12 presents a method of determining if a patient is a good candidate for right ventricular only pacing according to some embodiments of the present invention. Referring now to FIG. 12, the method beings by sensing the activation of atria in the patient. The timing of the activation is recorded as As 1202. Next, the right ventricle contraction time, RVs 1204, and the left ventricle contraction time, LVs 1206, are recorded. RVs 1204 and LVs 1206 contraction times may be directly or indirectly measured. Further As 1202, RVs 1204, and LVs 1206 may be determined using the timing of paced beats or intrinsic beats.

As 1202, RVs 1204, and LVs 1206, may be used to determine a patient's suitability for right ventricular only cardiac pacing. A patient may be a suitable candidate right ventricular only cardiac pacing therapy if the delay between As 1202 and RVs 1204 is greater than the delay between As 1202 and LVs 1206. If the delay from As 1202 to RVs 1204 is less than the delay from As 1202 to LVs 1204 (see e.g., FIG. 12 step 1208), the patient may not be a suitable candidate for right ventricular only cardiac pacing and the standard of care CRT should be performed 1210. Additionally right ventricular only cardiac pacing may not be suitable if the intrinsic As to LVs time is not less than a predetermined threshold 1212. The predetermined threshold may include, but is not limited to, 180 ms, 200 ms, 220 ms, or any other delay deemed appropriate for the patient.

Once a patient is identified as a candidate for right ventricular only cardiac pacing, a proper pacing time should be determined. In some embodiments of the present invention, the right ventricular only cardiac pacing occurs a determined amount of time after a sensed or paced atrial event. The atrioventricular delay time for right ventricular only pacing may be fixed or calculated. In some embodiments of the present invention, the atrioventricular delay for right ventricular only pacing occurs a fixed time after the sensed or paced atrial event determined as a percentage of the time between As 1202 and LVs 1206.

The optimal percentage of the time between As 1202 and LVs 1206 may be determined by evaluating the dyssynchrony and heterogeneity in the heart across a range of percentage delays. The time interval between atrial sensed or paced event and the left ventricular sensed event may be divided into several percentiles and the dyssynchrony and heterogeneity in the heart may be measured using multi-electrode ECG and methods disclosed above, during pacing the right ventricle only at atrioventricular delays equal to each of these percentile times.

Figure 13:
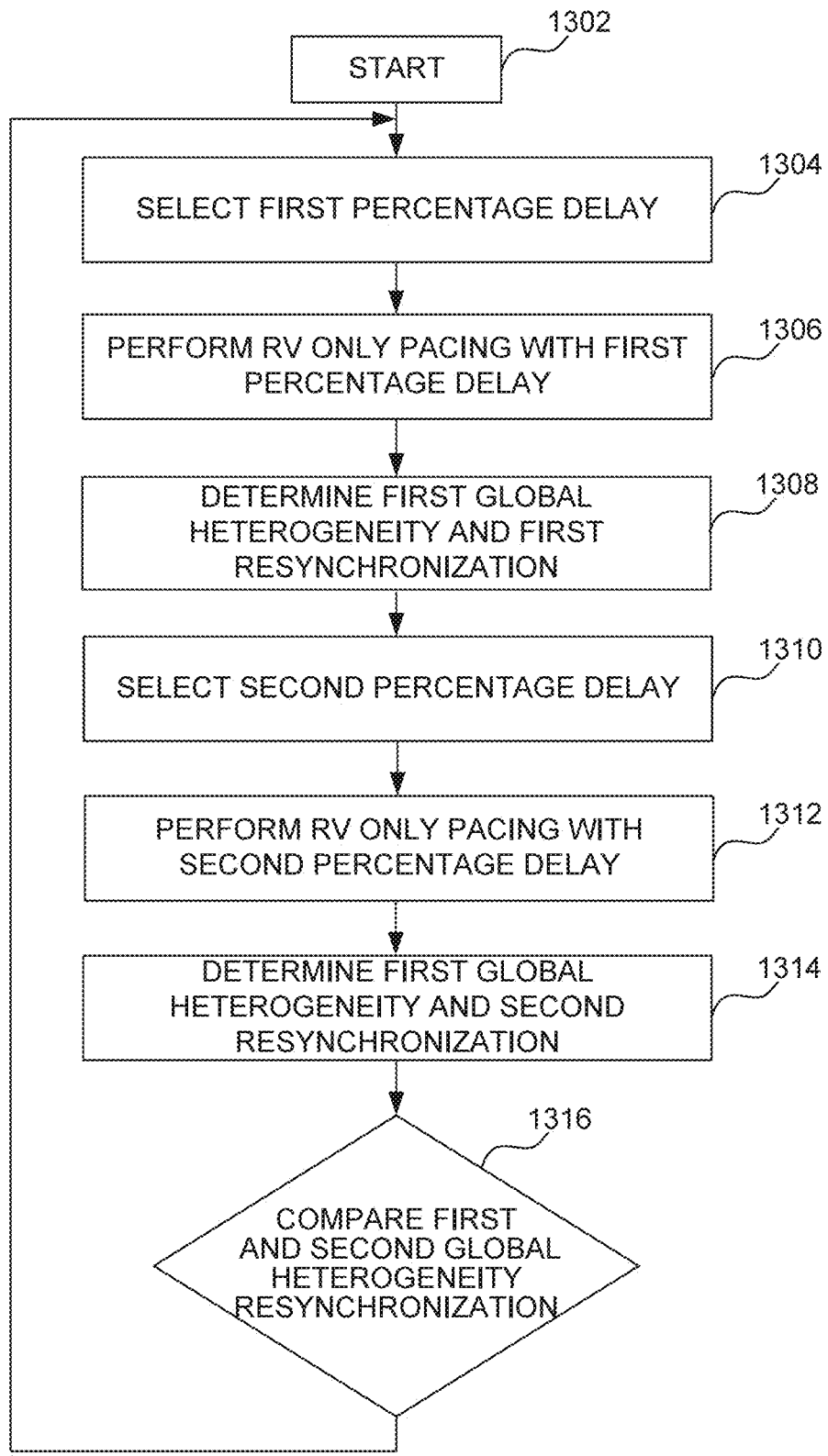
FIG. 13 is a flow diagram illustrating a technique for determining the optimal right ventricle pacing delay percentage according to some embodiments of the present invention.

According to some embodiments of the method, the optimal percentage for the right ventricular paced delay may be determined after first determining a patient's As 1202 and LVs 1206 (see, e.g. FIG. 12). Once a patient's As 1202 and LVs 1206 are recorded, a first percentage 1304 may be selected. For example, the percentage may be, but is not limited to 10% 15%, or 20%, 25%, 30%, 35%, 40%, 45%, 50%. The first percentage 1304 of the time delay between As 1202 and LVs 1206 is used to pace the patient's heart after a sensed atrial event (step 1308 in FIG. 13). That is, after a sensed atrial event, the patient's right ventricle is paced a period of time after the atrial event equal to a first percentage 1308 of the time delay between As 1202 and LVs 1206. For example, if the As 1202 to LVs 1206 delay is 180 ms, and the selected first percentage 1308 is 50%, the patient's right ventricle is paced 90 ms after the atrial event is sensed.

Figure 16:
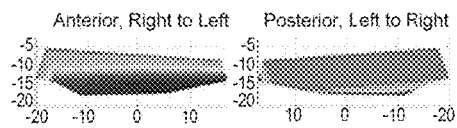
FIG. 16 is a set of graphical representations showing global electrical heterogeneity and resynchronization values of a heart determined using an ECG Belt according to some embodiments of the present invention.
Figure 16:
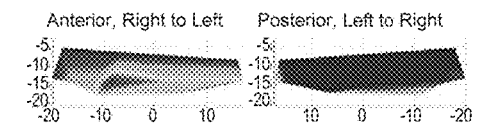
Figure 16:
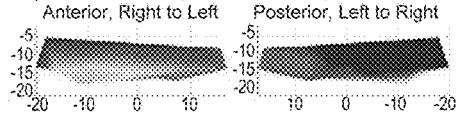
Figure 16:
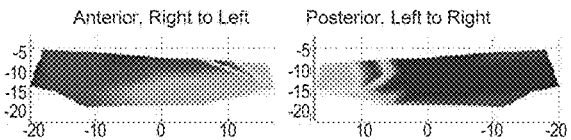
Figure 16:
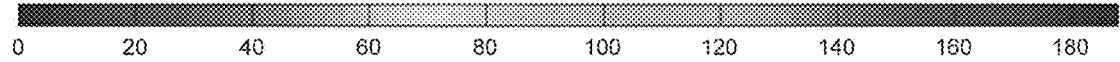

After the heart is paced with a specified right ventricle only percentage delay 1308, the global electrical heterogeneity of the heart and the resynchronization of the heart are determined using various systems or methods. The global electrical heterogeneity of the heart and the resynchronization of the heart may be shown on a map where the values may be plotted in a spatial dimension corresponding to the torso electric signals received by electrodes placed on the body of the patient. For example, FIG. 16 presents images showing electrical heterogeneity determined from the torso-electric signals received by the electrodes on a patent's torso. Each data point corresponds to the heterogeneity of the signal received by each electrode as compared with the set of received signals.

After the global electrical heterogeneity of the heart and the resynchronization of the heart are determined at a first percentage (50% in the example above), as second percentage is selected and the process is repeated. For example, a 60% RV-only delay may be selected as the second percentage. After the second percentage is selected, RV-only pacing is again used with the second percentage used as to determine the timing delay. After the RV-only pace is applied, the effects on the heart are again measured. Both the global electrical heterogeneity of the heart and the resynchronization of the heart are determined when the heart is paced with the second percentage.

Figure 14:
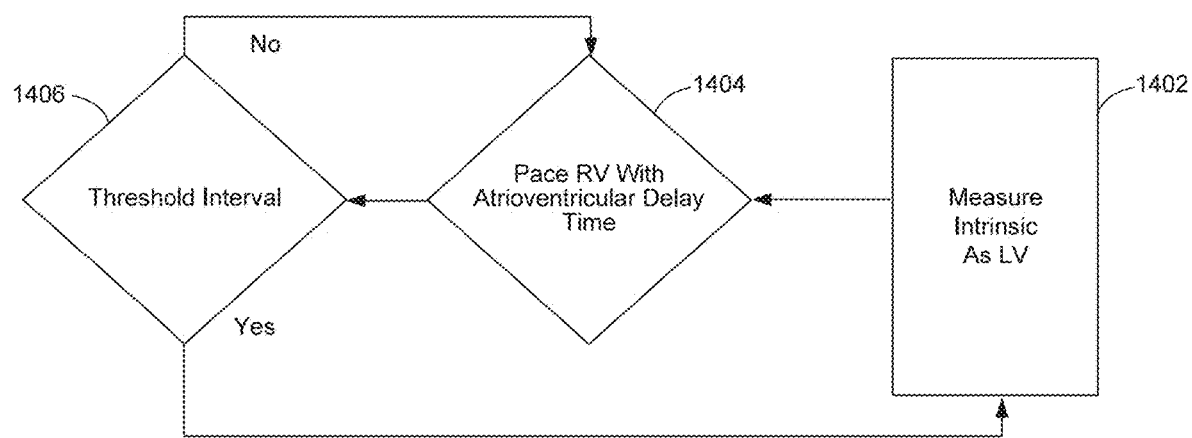
FIG. 14 is a flow diagram illustrating a technique of adaptively applying right ventricular only cardiac pacing according to some embodiments of the present invention.

This process may be repeated with various delay percentages. After each delay percentage is evaluated, the optimal delay percentage for the patient may be selected. The selected delay may be the delay that corresponds to the lowest global electrical heterogeneity of the heart and the resynchronization of the heart should be selected as this percentage reduces the overall stress on the heart and reduces the changes of heart failure or even death. The same process may be repeated during atrial pacing (instead of atrial sensing) and the optimal percentage (of atrial paced to LV sense) delay for delivering right ventricular only pacing following an atrial paced event may be determined. Additionally, other therapy parameters may be adjusted and the corresponding heterogeneity and resynchronization of the heart may be determined. As with optimizing right ventricular only pacing delay times, other therapy parameter conditions, such as the energy delivered or the pacing vector may be varied. For example, in one embodiment a device for pacing the patient's heart may adapt the right ventricular pacing time delay to account for changes in the intrinsic rhythm of the heart. FIG. 14 presents one embodiment of the present invention where the intrinsic As 1202 and intrinsic LVs 1206 is measured 1402 and the percent corrected right ventricular delay applied 1404 to pace the right ventricle is determined using the intrinsic As 1202 and intrinsic LVs 1206. After a threshold time 1406, for example one minute, the intrinsic As 1202 and intrinsic LVs 1206 are measured again withholding right ventricular pacing for one, two or three beats, and the updated time between the As 1202 and the LVs 1206 is used to determine the new atrioventricular delay for subsequent right ventricular only pacing by multiplying the optimal percentage with the updated delay between As and LVs.

Figure 9:
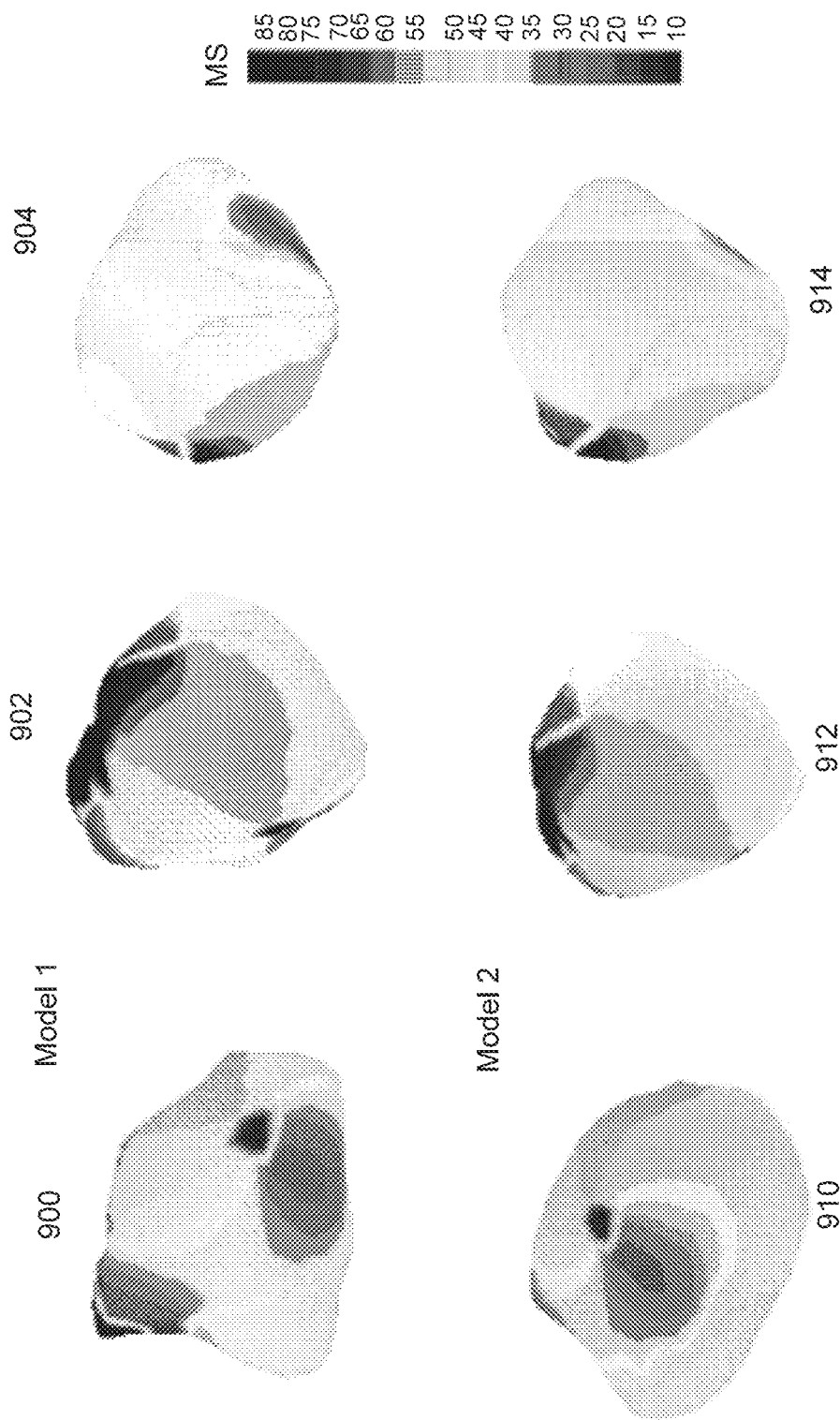
FIG. 9 is a series of isochrone maps of cardiac activation times constructed with two different heart-torso models using body-surface ECG data from the same patient.

FIG. 9 is a series of isochrones maps of cardiac activation times. Views 900, 902 and 904 were constructed using torso-surface potentials measured on the surface of the torso of a patient and projected onto three dimensional models of the torso and the heart of the patient. Views 910, 912, and 914 were constructed using the measured torso-surface potentials of the same patient projected onto a different model torso and model heart.

The three-dimensional representation of the hearts depicted in views 900, 902, 904, 910, 912 and 914 were constructed using computer tomography (CT) images of hearts obtained from databases of previously acquired cardiothoracic images. The locations of the electrodes, e.g., electrodes 404 of sensing device 400B (FIG. 4B), on the torso of the patient may be plotted to approximate locations on a model torso. A computer may be used to solve the inverse problem of electrocardiography, which includes determining the electrical activity on the surface of the heart that would produce the measured torso-surface potentials. The isochrones maps illustrated in views 900, 902, 904, 910, 912 and 914 are based on images of hearts of two different patients, which are also used to determine the geometry of the heart and relationship to the corresponding torso for solving the inverse problem of electrocardiography.

The model torsos and hearts may be constructed by manual or semi-automatic image segmentation from available databases of previously acquired medical images (CT/MRI) of cardiomyopathy patients using commercially available software. Each model may be discretized using boundary element method and may be further manipulated to account for patients with different physical characteristics (e.g., large frame, medium frame and small frame) and heart sizes (e.g., x-large, large, medium, small).

A user may select the appropriate model torso and heart to suit the patient, e.g., a patient having a large torso may be simulated with a large frame model torso. In some examples, medical images of the patient, e.g., CT or MRI images, may be manually or semi-automatically segmented, registered, and compared to a variety of available models for selection from amongst the models. One or more views of 2-D medical images (e.g., X-ray or fluoroscopy) may also be used. The user may project the measured torso-surface potentials from the torso of the patient onto the corresponding locations on the model torso. The inverse problem of propagating the electrical signals from the model torso to the model heart may then be solved, and activation times for the model heart may be estimated.

In one example in which the techniques of this disclosure were applied, human thoracic CT images for other subjects were obtained from image databases. Semi-automatic image segmentation was performed on the images to generate the three-dimensional representation of the different models of hearts and torsos. In some examples, image segmentation may be done with the AMIRA software package commercially-available from Visage Imaging, Inc., of San Diego, Calif.

For the example, the electrode locations on the model torso were approximate. In particular, the locations electrodes on the patient torso to the model torso the locations of the electrodes on the patient torso were projected onto the surface of the model torso based on the order in which the electrodes were mounted on the patient. For the purpose of this projection, the patient and model torsos were divided into right anterior, left anterior, right posterior and left posterior regions, using the sternum (anterior) and the spine (posterior) as references. Electrodes were arranged in vertical strips and three strips were applied to each region of the torso. Electrodes in these regions were projected on to the corresponding segments of the model torso. The method described is one of many techniques that may be used to registered or map the geometrical distribution of measured electrical potentials. For example, the measured electrical potentials may be interpolated and resampled at electrode positions given by the model. Projection of the electrode locations from segments of the patient torso onto the corresponding segments of the model torso in the correct order enabled the activation patterns and spatial dispersion of activation on the model heart to reflect the activation patterns and spatial dispersion of activation on the actual patient heart with relative accuracy. In one example, the inverse problem of electrocardiography may be solved using the Matlab regularization toolbox (Hansen P C, Regularization Tools: A Matlab package for analysis and solution of discrete ill-posed problems, Numerical Algorithms, 6 (1994), pp 1-35).

Input data-sets for solving the inverse problem consistent with the example may include multi-electrode surface ECG measurements, the 3-D Cartesian coordinates of the model heart and torso surfaces, and the mesh over each model surface which specified the connectivity of the different points on each surface. An output consistent with the techniques of this disclosure may include activation times on the 3-D model heart surface which can be visualized using visualization software and computer graphics tools. In some examples, the 3-D model heart surface may be visualized using the tools in Matlab (Mathworks Inc, Natick, Mass.) or more advanced visualization software, such as Tecplot (Tecplot Inc, Bellevue, Wash.).

Comparing estimated cardiac activation times on two different, both cardiac activation times determined from the same torso-surface potential signals for one subject, show similar patterns and distribution. For example, region 906 of views 902 and 904 corresponds in size and activation time to region 916 of views 912 and 914. Region 908 of views 902 and 904 corresponds to region 918 of views 912 and 914. Additionally, the standard deviations of activations time for both models are both derived from the same torso-surface potentials for one subject, were similar (17.6 and 15.5 ms). The overall pattern of cardiac activation and measures of dispersion of cardiac activation times are thus not dependent on a specific heart-torso model. Using a generic heart-torso model may allow a user to create an isochrones model of the cardiac activation time suitable for diagnosis and observation while avoiding expense, inconvenience, and radiation exposure that may be caused by the CT scan or other imaging that may be used to produce a patient-specific model of the heart of the patient.

Figure 10:
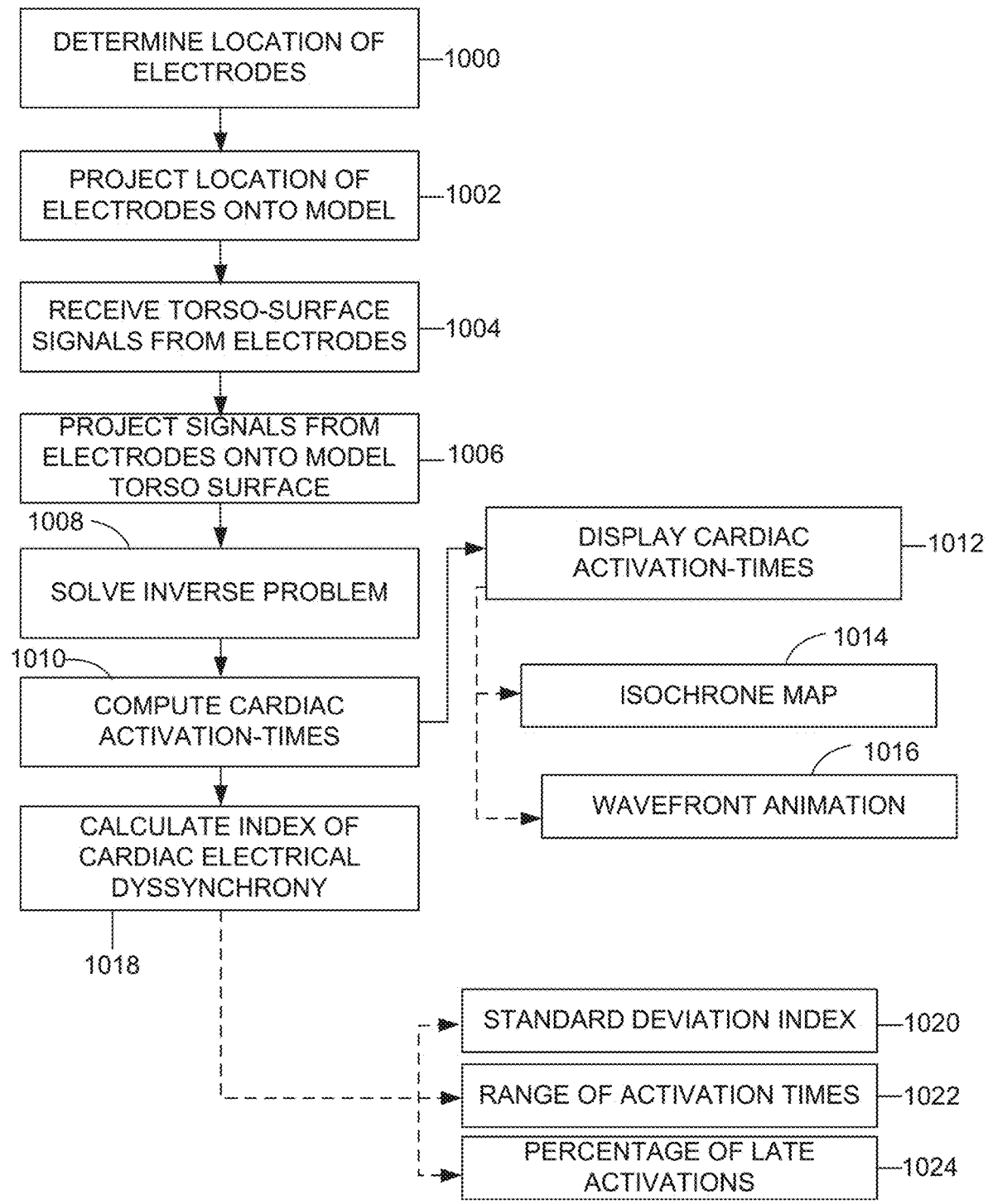
FIG. 10 is a flow diagram illustrating an example operation of a system to measure the cardiac electrical dyssynchrony of a patient via the cardiac activation times.

FIG. 10 is a flow diagram illustrating an example operation of a system to measure the cardiac electrical dyssynchrony of a patient via the cardiac activation times. Processing unit 500 determines the location of the electrodes 404, e.g., based on an analysis of imaging data by an electrode location registration module 524. Processing unit projects the locations of the electrodes onto a model torso, e.g., a selected model torso (1002).

A cardiac event, e.g., depolarization, occurs causing an electrical signal to propagate through the torso of the patient, and register on the electrodes distributed on the surface of the torso of the patient. The torso-surface potential signals sensed by the electrodes may be received by processing unit 500 (1004). The processing unit may project the signals onto the surface of the model torso based on the determined locations of the electrodes (1006).

The processing unit may solve the inverse problem of determining epicardial potentials based on torso-surface potentials (1008). The processing unit may then calculate cardiac activation times at a variety of locations of the model heart based upon the projected torso-surface potentials (1010). The cardiac activation times may be computed by, for example, determining the greatest negative slope of the epicardial electrogram potentials (1016) or by least squares minimization in the solution of the inverse problem (1018). The cardiac activation time may be displayed (1012). Examples of potential methods for displaying cardiac activation times include isochrone maps (1014) and a movie depicting the progression of the wavefront over the model heart (1016). The processing unit may be configured to allow a user select between, or display simultaneously, various display modes, including the wave front movie and isochrones maps. Additionally, one or more indices of cardiac electrical dyssynchrony may be calculated (1018), including the SDAT (1020), RAT (1022), and PLAT (1024).

For solving the inverse problem (1008), epicardial potentials may be computed from projected torso-surface potentials assuming a source-less volume conductor between the heart and the torso in an inverse Cauchy problem for Laplace's equation. Alternatively, an analytic relation between torso-surface potentials and the cardiac transmembrane potential may be assumed. Additionally, cardiac activation times may be estimated (1010) from the steepest negative slope of the epicardial electrograms determined from the inverse solution of the torso-surface potential/ epicardial potential transformation. In other examples, model torso-surface potentials may be simulated based on the analytic relationship approach to determining the cardiac transmembrane potential from torso-surface potential. Cardiac activation times (parameters in the analytic relationship) may be computed based on minimizing the least square difference between the projected model torso-surface potentials and simulated torso-surface potentials.

In some examples, the construction of a torso-surface activation times isochrone map (1014), wavefront animation (1016), or other graphical representation of cardiac electrical dyssynchrony, as well as the calculation of indices of cardiac electrical dyssynchrony (1018), may be performed for a particular region of the model heart based the computed cardiac activation times in such regions. Graphical representations and indices of cardiac electrical dyssynchrony may be determined for each of a plurality of regions based on the computed cardiac activation times in such regions. In some examples, the representations and indices for various regions may be presented together or compared.

Figure 11:
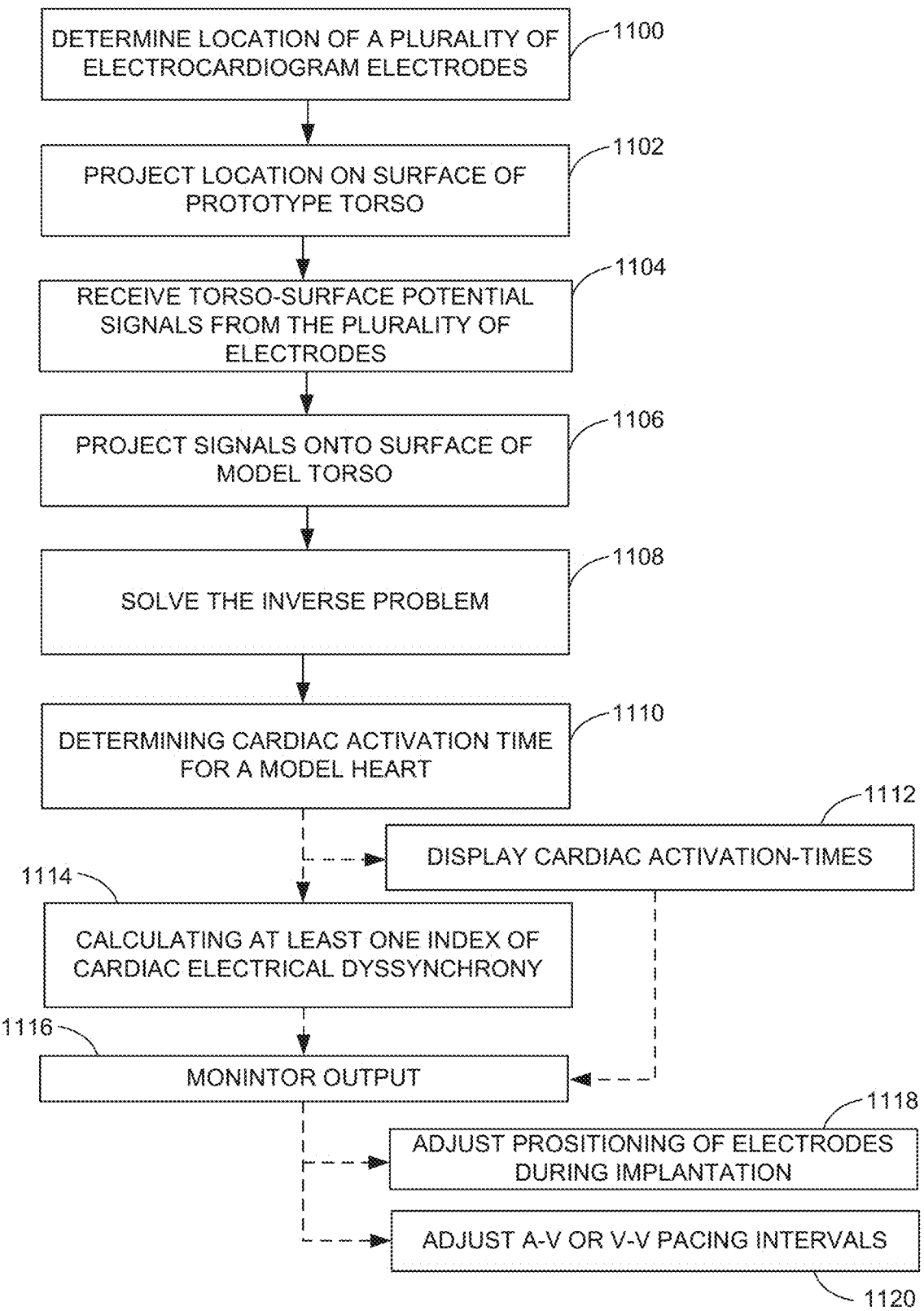
FIG. 11 is a flow diagram illustrating an example technique for configuring CRT based on an assessment of cardiac electrical dyssynchrony of a patient via the cardiac activation times.

FIG. 11 is a flow diagram illustrating an example technique for measuring the cardiac electrical dyssynchrony of a patient via determined cardiac activation times. The techniques may comprise determining the location of a plurality of electrodes (1100), projecting the location of the electrodes onto the surface of a model torso (1102), recording the output of the plurality of electrodes (1104), projecting the output of the plurality of the electrodes on the surface of the model torso (1106), solving the inverse problem (1108) and determining the cardiac activation times for a model heart from the projected torso-surface potentials (1110). The cardiac activation times may be displayed (1112). One or more indices of electrical dyssynchrony may be calculated (1114). The output, the indices of cardiac electrical dyssynchrony and cardiac activation time maps, may be monitored, allowing a user to diagnose the patient, adjust the position of CRT electrodes during implantation (1118), or adjust A-V or V-V pacing intervals of the CRT device (1120).

A user may monitor the output of the calculations (1116), e.g., the at least one indices of cardiac electrical dyssynchrony or the display of cardiac activation times. Monitoring these values may allow the user to diagnose a condition that might benefit from CRT or to evaluate the effectiveness of CRT. For example, the at least one index of cardiac electrical dyssynchrony may indicate the presence of damage to electrical conductivity of the heart of the patient, for example the presence of a left or right bundle branch block, that may not be apparent from the examination of a standard 12 lead ECG readout. A large SDAT indicates that the activation of the ventricles is occurring over a large time span, indicating that the depolarization of the ventricles is not occurring simultaneously. A large RAT also indicates a broad range of activation times and asynchronous contraction of the ventricles. A high PLAT may indicate that a specific region of the heart, e.g., the posterior regions more associated with the left ventricle, is failing to activate in concert with the measured QRS complex.

The user may adjust the positioning of CRT electrodes, e.g., electrodes 108, 110, and 112 of IMD 100 (FIG. 1) according to the displayed cardiac activation times or the indices of cardiac electrical dyssynchrony. For example, the processing unit, via a display, may implement systems that displays shifting colors based on the percentage change of the indices of cardiac electrical dyssynchrony. As the position of the CRT electrodes are adjusted (1118), the displayed colors may shift from red to yellow to green based on the percentage improvement of the indices of cardiac electrical dyssynchrony. This may allow a user to rapidly determine if the adjustments of the CRT electrodes are having a positive effect on the symptoms of the patient. In another example, the user may adjust the A-V or V-V pacing intervals of an implanted CRT device (118). The minimum value of the indices of cardiac electrical dyssynchrony may indicate adequate pacing intervals. Isochrone maps or wave front propagation movies may also be used to aid in CRT adjustments or to diagnose conditions that may be responsive to CRT treatment.

Figure 15:
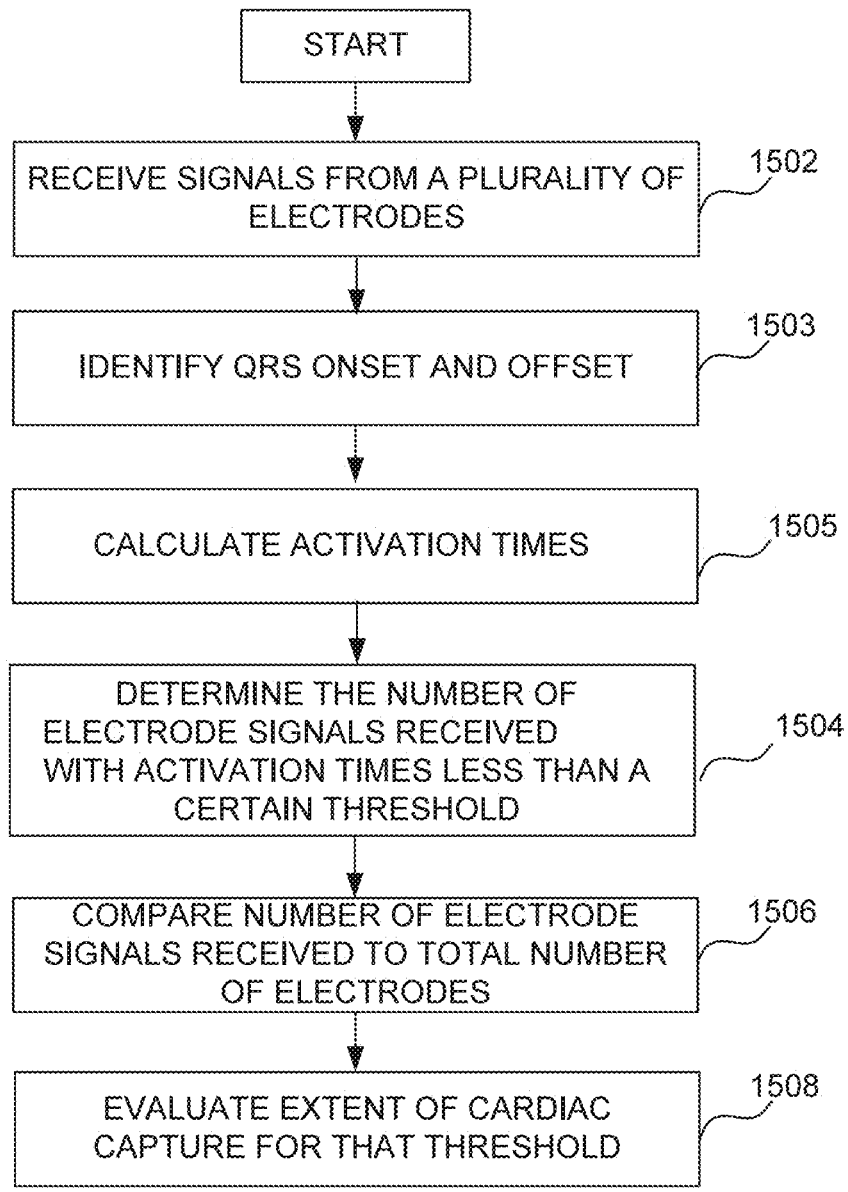
FIG. 15 is a flow diagram illustrating a technique for determining the extent of applied cardiac stimulation according to some embodiments of the present invention.

Further, the extent of applied cardiac stimulation after the heart is paced may be determined by comparing the number of electrodes that activate before a predetermined time from the onset of the activation process. This comparison can be utilized to estimate the extent of cardiac tissue capture from the pacing event. The amount of capture in localized areas of the heart may be determined if the location of the electrodes is correlated to specific parts of the heart. For example, FIG. 15 presents a flow diagram detailing a method according to one embodiment of the invention for determining the extent of cardiac tissue stimulation. The method begins when torso-potential signals are received by electrodes 1502 on the patent. The approximate onset of ventricular depolarization may be identified by the earliest onset of QRS complex on any torso-lead. Similarly the approximate offset may be determined by the latest offset of QRS complex on any torso-lead.

Activation times are determined at each electrode within the detected onset and offset of a QRS complex. The number of electrodes with activation times earlier than a predetermined time threshold from the onset of the corresponding depolarization (QRS) complex is determined. In another embodiment the number of electrodes with activation times earlier than a predetermined time-threshold from the earliest detected activation-time may be determined. The threshold may be 5 ms, 10 ms, 15 ms, 20 ms. For example, the threshold may exclude signals that are received by the electrodes more than 20 ms after a paced or intrinsic beat. The number of activated electrodes activating earlier than the pre-determined threshold is then compared to the total number of electrodes 1506 to determine the extent of applied cardiac tissue stimulation 1508. The extent of applied cardiac tissue stimulation may be determined using a paced or an intrinsic beat of the heart. If a pace beat is used, care should be taken to avoid interference with the intrinsic beat of the heart. In some embodiments, avoiding interference with the intrinsic beat of the heart may take the form of pacing the heart with a very short atrioventricular interval (less than 50 ms) thereby electrically activating the entire heart by pacing without any contribution of the intrinsic electrical conduction of the heart. In the absence of regular one-to-one atrioventricular conduction, interference with the intrinsic beat may be avoided by pacing the heart rapidly. Determining the extent of tissue capture may be performed by applying different magnitudes of the predetermined threshold, for example, 10 ms and 20 ms. Different extents of tissue capture may be determined for the interval between the two time-thresholds, indicating the speed at which electrical activations spreads. For example if 5% of electrodes activate earlier than 10 ms and 20% activate earlier than 20 ms, the differential extent of capture during the interval from 10 ms to 20 ms from onset of depolarization will be 15%. This information may be helpful as speed of propagation of electrical activation may vary with time during the depolarization cycle. In one embodiment, the speeds of cardiac conduction may be determined applying different timing thresholds throughout the entire QRS complex to determine an average rate of change of propagation speed over the depolarization cycle.

As indicated above, to facilitate evaluating the whether a patient is a candidate for CRT based on the monitored output (1116), the one or more indications of cardiac electrical dyssynchrony, e.g., indices or graphical indications, may be determined based on torso-surface activation times during both intrinsic conduction of the heart, and during CRT. Differences between the indications during intrinsic conduction and CRT may indicate that CRT would provide benefit for the patient, e.g., that the patient is a candidate for CRT. Furthermore, during implantation or a follow-up visit, the one or more indications of cardiac electrical dyssynchrony may be determined for each of a plurality of lead positions, electrode configurations, or other parameter values based on torso-surface activation times resulting from delivery of CRT at the positions, or with the electrode configurations or parameter values. In this manner, differences between cardiac electrical dyssynchrony indications associated with various locations, electrode configurations, or parameter values may be compared to determine preferred locations, configurations, or values.

Various examples of this disclosure have been described. However, one of ordinary skill in the art will appreciate that various modifications may be made to the described embodiments without departing from the scope of the claims. For example, although SDAT, RAT and PLAT have been discussed as example statistical indices of the dispersion of activation times, other indices or metrics of the dispersion of the timing of depolarization may be determined according the techniques of this disclosure. As one example, a range of activation times between two specific regions, e.g., anterior and posterior, may be determined. As another example, a range or variability of activation times after excluding certain locations or regions may be determined according to the techniques of this disclosure. The excluded locations or regions may be those that are believed to be scar tissue, e.g., identified by low amplitude electrical signals, or locations or regions that are beyond the extent of the far-field QRS complex. In general, calculation of an index may include determining any statistical or other value based on the torso-surface or cardiac activation times, or some subset thereof. These and other examples are within the scope of the following claims.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A method of determining an extent of applied cardiac tissue capture due to pacing comprising:
    applying external electrodes on a patient's torso to noninvasively monitor electrical activity;
    pacing the patient's cardiac tissue;
    noninvasively measuring, without use of an implantable electrode, torso-surface potential signals detected by the external electrodes, wherein the torso-surface potential signals are representative of depolarization of cardiac tissue that propagates through the torso of the patient;
    determining an activation time for each electrode of the external electrodes based on the noninvasively measured torso-surface potential signals;
    determining a number of external electrodes that register an activation time that meets a predetermined pacing capture criteria;
    calculating a pacing capture percentage index by dividing the number of the external electrodes that registered an activation time that meets the predetermined pacing capture criteria by a total number of the external electrodes distributed on the patient's torso; and
    determining the extent of applied cardiac tissue capture due to the pacing based on the pacing capture percentage index, wherein the extent of applied cardiac tissue is indicative of the amount of cardiac tissue captured by the pacing.

2. The method of claim 1, wherein the pacing of the patient's cardiac tissue is timed to avoid interference with an intrinsic rhythm of the heart.

3. The method of claim 1, wherein the predetermined criteria comprises a predetermined activation time threshold.

4. The method of claim 1, wherein the predetermined criteria comprises a predetermined time period within which the activation times of the external electrodes must be registered.

5. The method of claim 4, wherein the predetermined time period is about 5 ms, 10 ms, 15 ms, or 20 milliseconds from a specified time origin where the specified time origin is an earliest activation time detected for a corresponding depolarization cycle.

6. The method of claim 4 wherein the predetermined time period is a percentile of the activation times registered by the external electrodes.

7. The method of claim 1, further comprising adjusting a therapeutic parameter value based on the extent of applied cardiac tissue capture due to the pacing.

8. The method of claim 7, wherein the therapeutic parameter comprises a magnitude of energy applied by a pacing source.

9. The method of claim 7, wherein the therapeutic parameter comprises a direction of a pacing vector applied by a pacing source.

10. The method of claim 9, wherein the pacing source comprises a pacing device, wherein the direction of the pacing vector is determined from a geometry of the pacing device.

11. A system to determine an extent of applied cardiac tissue capture due to pacing, the system comprising:
    external electrodes to be distributed on a patient's torso to noninvasively monitor electrical activity;
    a pacing device comprising at least one pacing electrode to stimulate the patient's cardiac tissue; and a processing unit comprising one or more processors and operably coupled to the external electrodes, the processing unit configured to:
noninvasively measure, without use of an implantable electrode, torso-surface potential signals detected by the external electrodes, wherein the torso-surface potential signals are representative of depolarization of cardiac tissue that propagates through the torso of the patient;
determine an activation time for each external electrode of the external electrodes based on the noninvasively measured torso-surface potential signals;
determine a number of the external electrodes that register an activation time that meet a predetermined pacing capture criteria;
calculate a pacing capture percentage index by dividing the number of the external electrodes that registered activation times that meet the pacing capture predetermined criteria by a total number of the external electrodes distributed on the patient's torso; and
determine the extent of applied cardiac tissue capture due to the pacing based on the pacing capture percentage index, wherein the extent of applied cardiac tissue is indicative of the amount of cardiac tissue capture by the pacing.

12. The system of claim 11, wherein the distributed external electrodes comprise at least 20 electrodes.

13. The system of claim 11, wherein the pacing device is implanted in the patient and comprises a lead in direct contact with the patient's cardiac tissue.

14. The system of claim 13, wherein the pacing device comprises the processing unit.

15. The system of claim 13, wherein the pacing device comprise two electrodes located on the same lead.

16. The system of claim 11, wherein the pacing device comprises an external ultrasound delivery device comprising an ultrasound transducer to apply the pacing using an ultrasound wave.

17. A method of determining an extent of applied cardiac tissue capture due to pacing comprising:
applying stimulation to a patient's cardiac tissue and receiving potential signals noninvasively detected at a first time period, wherein the potential signals are representative of depolarization of cardiac tissue that propagates through the torso of the patient;
determining a first extent of applied cardiac tissue capture due to pacing based on activation times derived from the noninvasively detected potential signals received at the first time period;
adjusting a therapeutic parameter related to the application of the stimulation to the patient's cardiac tissue based on the determined extent of applied cardiac tissue capture due to the pacing, in order to meet a predetermined treatment goal;
applying stimulation to the patient's cardiac tissue and receiving potential signals noninvasively detected at a second time period, wherein the potential signals are representative of depolarization of cardiac tissue that propagates through the torso of the patient;
determining a second extent of applied cardiac tissue capture due to the pacing based on the noninvasively detected potential signals received at the second time period, wherein each of the first and second extent of applied cardiac tissue is indicative of the amount of cardiac tissue capture by the pacing; and
determining if the adjustment of the therapeutic parameter resulted in meeting the predetermined treatment goal based on the first extent of applied cardiac capture due to the pacing and the second extent of applied cardiac capture due to the pacing.

18. The method of claim 17, wherein the therapeutic parameter is a magnitude of energy applied by a pacing source.

19. The method of claim 17, wherein the therapeutic parameter is a direction of a pacing vector applied by a pacing source.

20. The method of claim 19, wherein the pacing source comprises a pacing device, wherein the direction of the pacing vector is determined from a geometry of the pacing device applying the stimulation.

21. The method of claim 17, wherein the therapeutic parameter is a timing interval between successive stimulations of the patient's cardiac tissue.

22. The method of claim 17, wherein the predetermined treatment goal comprises increasing the extent of applied cardiac tissue capture due to the pacing within a predetermined time period.

23. The method of claim 17, wherein the predetermined treatment goal comprises decreasing the extent of applied cardiac tissue capture due to the pacing within a predetermined time period.

24. A system to determine an extent of applied cardiac tissue capture due to pacing, the system comprising:
external electrodes configured to be distributed on a patient's torso to noninvasively monitor electrical activity;
means for stimulating the patient's cardiac tissue;
means for noninvasively measuring, without use of an implantable electrode, torso-surface potential signals detected by the external electrodes, wherein the torso-surface potential signals are representative of depolarization of cardiac tissue that propagates through the torso of the patient;
means for determining an activation time for each external electrode of the external electrodes based on the noninvasively measured torso-surface potential signals;
means for determining a number of the external electrodes that register an activation time that meet a predetermined pacing capture criteria;
means for calculating a pacing capture percentage index by dividing the number of the external electrodes that registered activation times that meet the predetermined pacing capture criteria by a total number of the external electrodes distributed on the patient's torso; and
means for determining the extent of applied cardiac tissue capture due to the pacing based on the pacing capture percentage index, wherein the extent of applied cardiac tissue is indicative of the amount of cardiac tissue capture by the pacing.

25. The system of claim 24, wherein the means for stimulating the patient's cardiac tissue is implanted in the patient.

26. The system of claim 24, wherein the means for stimulating the patient's cardiac tissue is external to the patient's body.

27. A method of determining an extent of applied cardiac tissue capture due to pacing comprising:
applying external electrodes on a patient's torso to noninvasively monitor electrical activity;
pacing the patient's cardiac tissue, wherein the pacing of the cardiac tissue is timed to avoid interference with the intrinsic rhythm of the patient's heart;

receiving torso-surface potential signals noninvasively detected by the external electrodes, wherein the torso-surface potential signals are representative of depolarization of cardiac tissue that propagates through the torso of the patient;

determining an activation time for each electrode of the external electrodes based on the torso-surface potential signals;

determining a number of the external electrodes that register an activation time that meets a predetermined pacing capture criteria;

calculating a pacing capture percentage index by dividing the number of the external electrodes that registered an activation time that meets the predetermined pacing capture criteria by a total number of the external electrodes distributed on the patient's torso, wherein the pacing capture predetermined criteria comprises a predetermined time period within which the activation times of the external electrodes must be registered; and determining the extent of applied cardiac tissue capture due to the pacing based on the pacing capture percentage index, wherein the extent of applied cardiac tissue is indicative of the amount of cardiac tissue capture by the pacing.

* * * * *